US008881723B2

(12) United States Patent
Frater

(10) Patent No.: US 8,881,723 B2
(45) Date of Patent: Nov. 11, 2014

(54) BREATHABLE GAS SUPPLY APPARATUS

(75) Inventor: Robert H. Frater, Lindfield (AU)

(73) Assignee: ResMed Limited, Bella Vista (AU)

( * ) Notice: Subject to any disclaimer, the term of this patent is extended or adjusted under 35 U.S.C. 154(b) by 3277 days.

(21) Appl. No.: 10/270,611

(22) Filed: Oct. 16, 2002

(65) Prior Publication Data
US 2004/0074494 A1    Apr. 22, 2004

(51) Int. Cl.
*A61M 16/00* (2006.01)
*A62B 7/00* (2006.01)
*A61M 16/06* (2006.01)
*A61M 16/20* (2006.01)

(52) U.S. Cl.
CPC ... *A61M 16/0072* (2013.01); *A61M 2205/8275* (2013.01); *A61M 16/06* (2013.01); *A61M 2205/8206* (2013.01); *A61M 16/20* (2013.01)
USPC ................. 128/204.18; 128/848; 128/204.28; 128/205.16; 128/205.18

(58) Field of Classification Search
CPC ............ A61M 16/0075; A61M 16/00; A61M 16/0078
USPC ............. 128/204.18, 204.22, 204.26, 205.12, 128/205.24, 205.25, 207.12, 202.29, 128/203.11; 482/13
See application file for complete search history.

(56) References Cited

U.S. PATENT DOCUMENTS

| | | | |
|---|---|---|---|
| 3,106,204 A | | 10/1963 | Paramelle |
| 3,216,413 A | * | 11/1965 | Arecheta Mota ........ 128/205.13 |
| 3,316,905 A | * | 5/1967 | Seeler ...................... 128/204.28 |
| 3,556,095 A | * | 1/1971 | Ismach .................... 128/204.28 |
| 3,557,785 A | * | 1/1971 | McQueen ................ 128/205.16 |
| 3,932,066 A | * | 1/1976 | Eyrick et al. ................... 417/328 |
| 4,163,448 A | * | 8/1979 | Grouard ................... 128/204.26 |
| 5,029,578 A | * | 7/1991 | Swiatosz .................. 128/202.26 |
| 5,111,809 A | * | 5/1992 | Gamble et al. ........... 128/204.18 |

(Continued)

FOREIGN PATENT DOCUMENTS

| | | |
|---|---|---|
| DE | 1 491 776 | 5/1969 |
| GB | 798250 | 7/1958 |

(Continued)

OTHER PUBLICATIONS

Partial European Search Report for Corresponding EP Appln. No. 03 02 3326, Completed Feb. 23, 2004, 4 pgs.

(Continued)

*Primary Examiner* — Darwin Erezo
*Assistant Examiner* — Michael Mendoza
(74) *Attorney, Agent, or Firm* — Nixon & Vanderhye P.C.

(57) ABSTRACT

A breathable gas supply apparatus for a patient features a breathable gas supply system and a respiratory mask assembly in communication with the breathable gas supply system. The breathable gas supply system provides a supply of breathable gas to the respiratory mask assembly and removes a supply of exhaled gas from the respiratory mask assembly. The breathable gas supply system includes a housing having an inspiration chamber and an exhalation chamber and a movable structure in communication with the inspiration and exhalation chambers. The movable structure moves in phase with a respiratory cycle of a patient. In one preferred embodiment, the breathable gas supply system includes a second movable structure, which moves in response to a phase of the respiratory cycle of the patient. In another one preferred embodiment, the breathable gas supply system is powered to assist the patient's respiratory effort.

34 Claims, 33 Drawing Sheets

(56) References Cited

U.S. PATENT DOCUMENTS

| | | | |
|---|---|---|---|
| 5,628,305 A * | 5/1997 | Melker | 128/202.29 |
| 5,649,533 A | 7/1997 | Oren | |
| 6,123,069 A * | 9/2000 | Davis | 128/202.26 |
| 6,371,112 B1 | 4/2002 | Bibi | |
| 6,523,538 B1 * | 2/2003 | Wikefeldt | 128/204.18 |
| 6,595,212 B1 | 7/2003 | Arnott | |
| 6,626,175 B2 * | 9/2003 | Jafari et al. | 128/204.21 |
| 2001/0015203 A1 * | 8/2001 | Cumming | 128/204.26 |
| 2002/0104541 A1 | 8/2002 | Bibi et al. | |

FOREIGN PATENT DOCUMENTS

| | | |
|---|---|---|
| GB | 847280 | 9/1960 |
| GB | 1 157 331 | 7/1969 |
| JP | 2002-200168 A * | 7/2002 |
| WO | WO 03/105720 | 12/2003 |

OTHER PUBLICATIONS

European Search Report issued in EP Appln. No. 08150069.6 (Jun. 1, 2010).

Office Action issued in European Appln. No. 08150069.6 (Jun. 16, 2010).

* cited by examiner

BREATHABLE GAS SUPPLY APPARATUS

BACKGROUND

1. Field of Invention

The present invention relates generally to a breathable gas supply apparatus for use in respiratory therapy. More specifically, the invention provides a breathable gas supply apparatus and method for supplying breathable gas to a patient for treatment of various disorders including, but not limited to Obstructive Sleep Apnea (OSA), where a breathing 'splint' has proven to be useful.

2. General Background and Related Art

Treatments of OSA and other respiratory treatments are well known in the art. Generally, Continuous Positive Airway Pressure (CPAP) systems are used for either the treatment of OSA or the application of assisted ventilation for other purposes. Assisted ventilation is typically provided by an externally powered device including a flow generator and a flow delivery system including a mask worn by the patent.

As taught in Sullivan, U.S. Pat. No. 4,944,310, many patients need a low to moderate level of breathing assistance. A flow generator and air circuit provide a moderate level of positive airway pressure that prevents the patient's airway from collapsing. Such patients are necessarily restricted to sleeping in places that have external commercial or alternative power available to operate their breathing assistance machinery. Also, in the case of an electrical power outage the opportunity for treatment is denied.

Consequently, there is a need to provide a breathing assistance apparatus for those patients who need or want additional freedom from external reliance upon commercial or alternative power.

SUMMARY OF THE INVENTION

One aspect of embodiments of the present invention is to provide a breathing assistance apparatus for those patients who need or want additional freedom from external reliance upon commercial or alternative power. Another aspect of embodiments of the present invention is to provide a breathable gas supply apparatus for a patient that is responsive to a phase of a respiratory cycle of the patient. Yet another aspect of embodiments of the present invention is to provide a method of providing a source of pressurized breathable gas to the patient.

In one preferred embodiment, a breathable gas supply apparatus for a patient features a breathable gas supply system and a respiratory mask assembly in communication with the breathable gas supply system. The breathable gas supply system provides a supply of breathable gas to the respiratory mask assembly and removes a supply of exhaled gas from the respiratory mask assembly. The breathable gas supply system comprises a housing having an outer wall configured to define an air chamber and a first movable structure, which moves within the air chamber in phase with the respiratory cycle of the patient.

In another preferred embodiment, a method of providing a source of pressurized breathable gas to a patient is provided. The method comprises storing mechanical work done by the patient during an exhalation phase of the respiratory cycle of the patient and utilizing only the stored mechanical work to assist patient respiratory effort during an inhalation phase of the respiratory cycle of the patient.

In another preferred embodiment, a breathable gas supply apparatus for a patient is provided. The breathable gas supply apparatus for a patient comprises storing structure for storing mechanical work done by the patient during an exhalation phase of the respiratory cycle of the patient and utilizing structure for utilizing only the stored mechanical work to assist patient respiratory effort during an inhalation phase of the respiratory cycle of the patient.

In another preferred embodiment, a breathable air supply apparatus for a patient is provided that comprises a breathable gas supply system comprising a housing having an outer wall configured to define an air chamber and a first movable structure movable in the air chamber during the respiratory cycle of the patient. The first movable structure is configured to be capable of storing mechanical energy during an exhalation phase of the respiratory cycle of the patient and to be capable of transferring the stored mechanical energy to the patient during an inhalation phase of the respiratory cycle of the patient to assist the patient's respiratory effort.

In another preferred embodiment, a breathable air supply apparatus for a patient is provided that comprises first, second and third sealing structures, each being movable in response to a fluid pressure in a first direction to an open position and being movable in response to a fluid pressure in the opposite direction to a closed position, wherein the closed position prevents fluid flow through an associated conduit. A pressure actuator assembly is positioned in an air chamber defined by an outer wall of the apparatus. The pressure actuator assembly includes a first movable structure and a second movable structure, each being movable in response to fluid pressure. Movement of the first and second movable structures in a common direction allows (1) exhaled gas to be received into the air chamber from the respiratory mask assembly and (2) breathable gas to be received into the air chamber. Movement of the first and second movable structures in a direction opposite the common direction allows (1) exhaled gas to exit the apparatus through a vent formed therein to the atmosphere and (2) breathable gas to be received in the respiratory mask assembly.

In another preferred embodiment, a breathable air supply apparatus for a patient is provided that comprises a breathable gas supply system that is responsive to a phase of the respiratory cycle of the patient and that is powered to assist the patient's respiratory effort.

In another preferred embodiment, a breathable gas supply apparatus for a patient is provided that comprises an upper moveable member, a lower member and a fluid supply. The upper member has an inner wall and an outer wall and the lower member is in communication with the upper member. The lower member has an inner wall structure surrounding the inner wall of the upper member and an outer wall structure surrounding the outer wall of the upper member. The fluid supply is in communication with the inner wall and the inner wall structure and is in communication with the outer wall and the outer wall structure.

Other aspects, features and advantages of the present invention will become apparent from the following detailed description and the accompanying drawings.

DETAILED DESCRIPTION OF PREFERRED EMBODIMENTS

Figure 1:
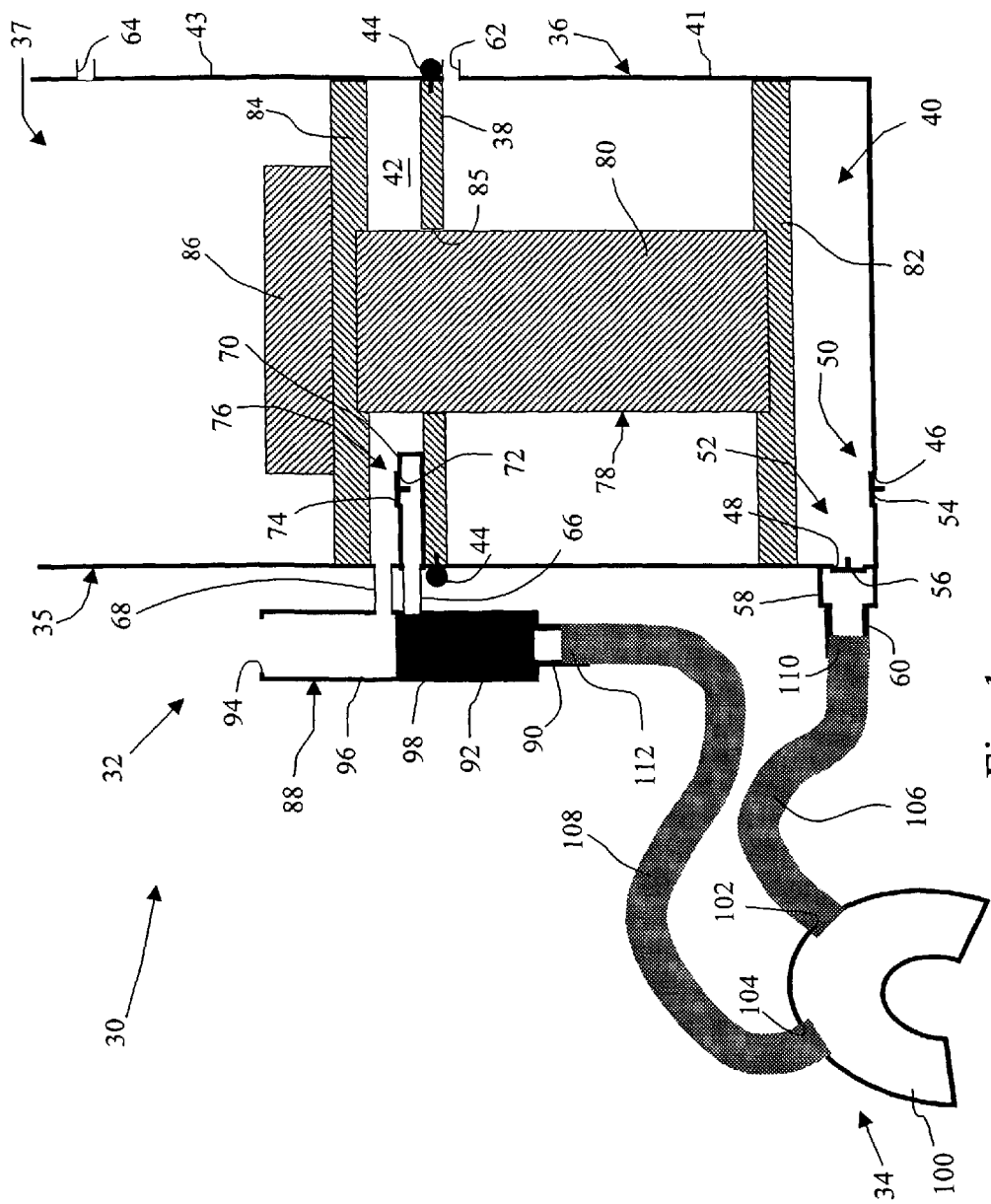
FIG. 1 is a schematic view of a breathable gas supply apparatus in an initial position thereof according to one embodiment of the present invention.
Figure 2:
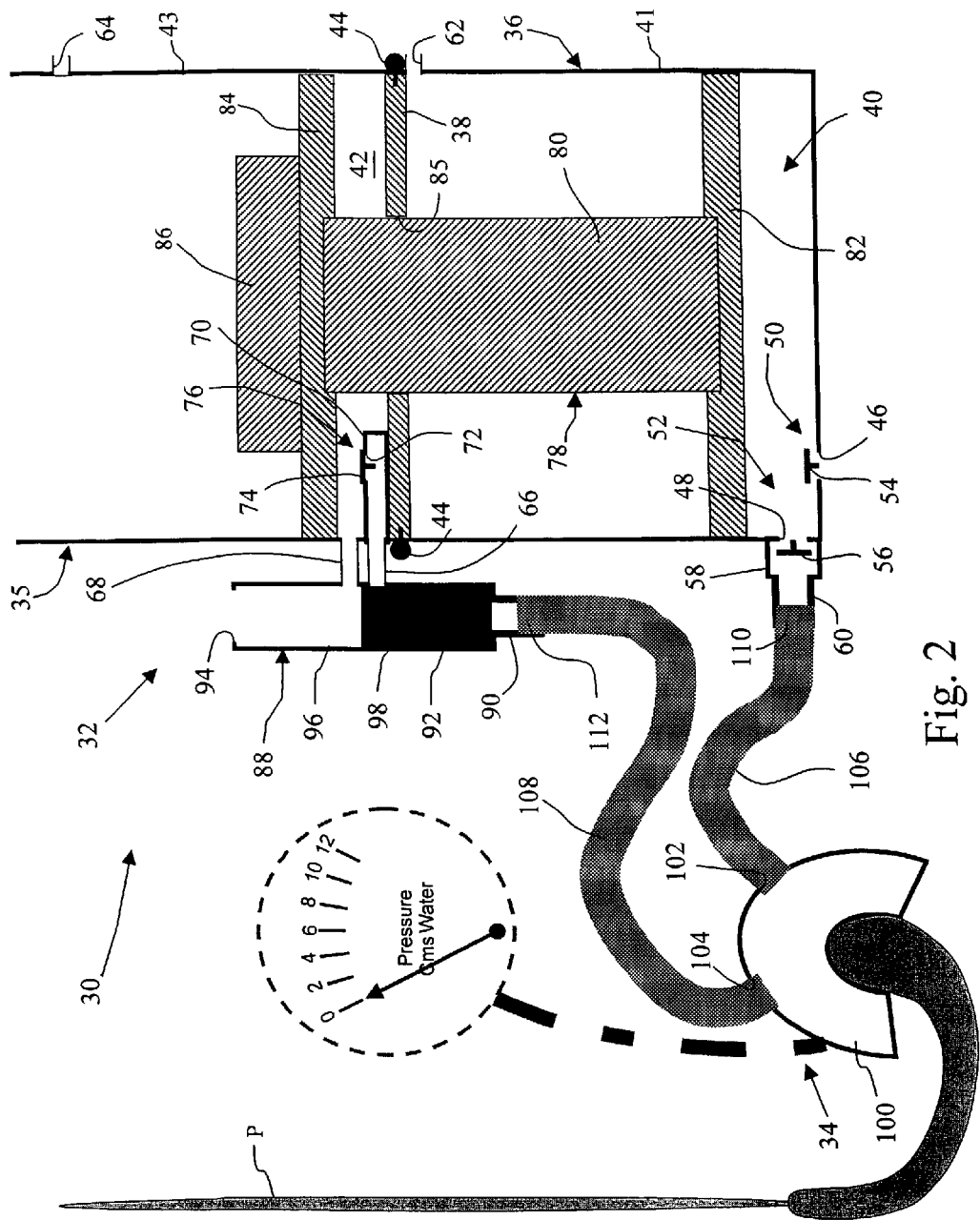
FIGS. 2-6 are schematic views of the breathable gas supply apparatus shown in FIG. 1 during subsequent initial inhalation positions thereof, wherein the patient is inhaling breathable gas from the atmosphere through the first and second air supply valves, respectively.
Figure 3:
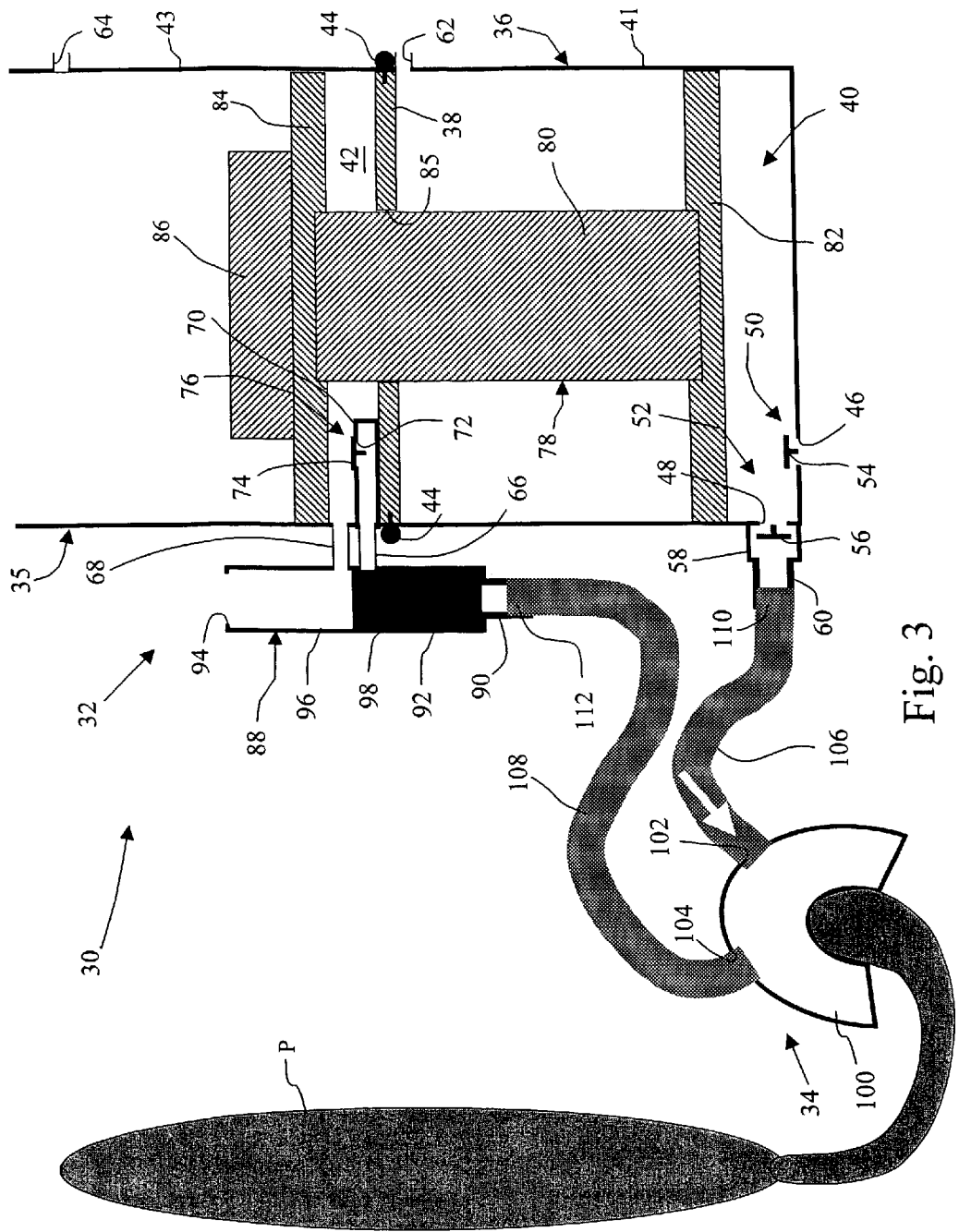
Figure 4:
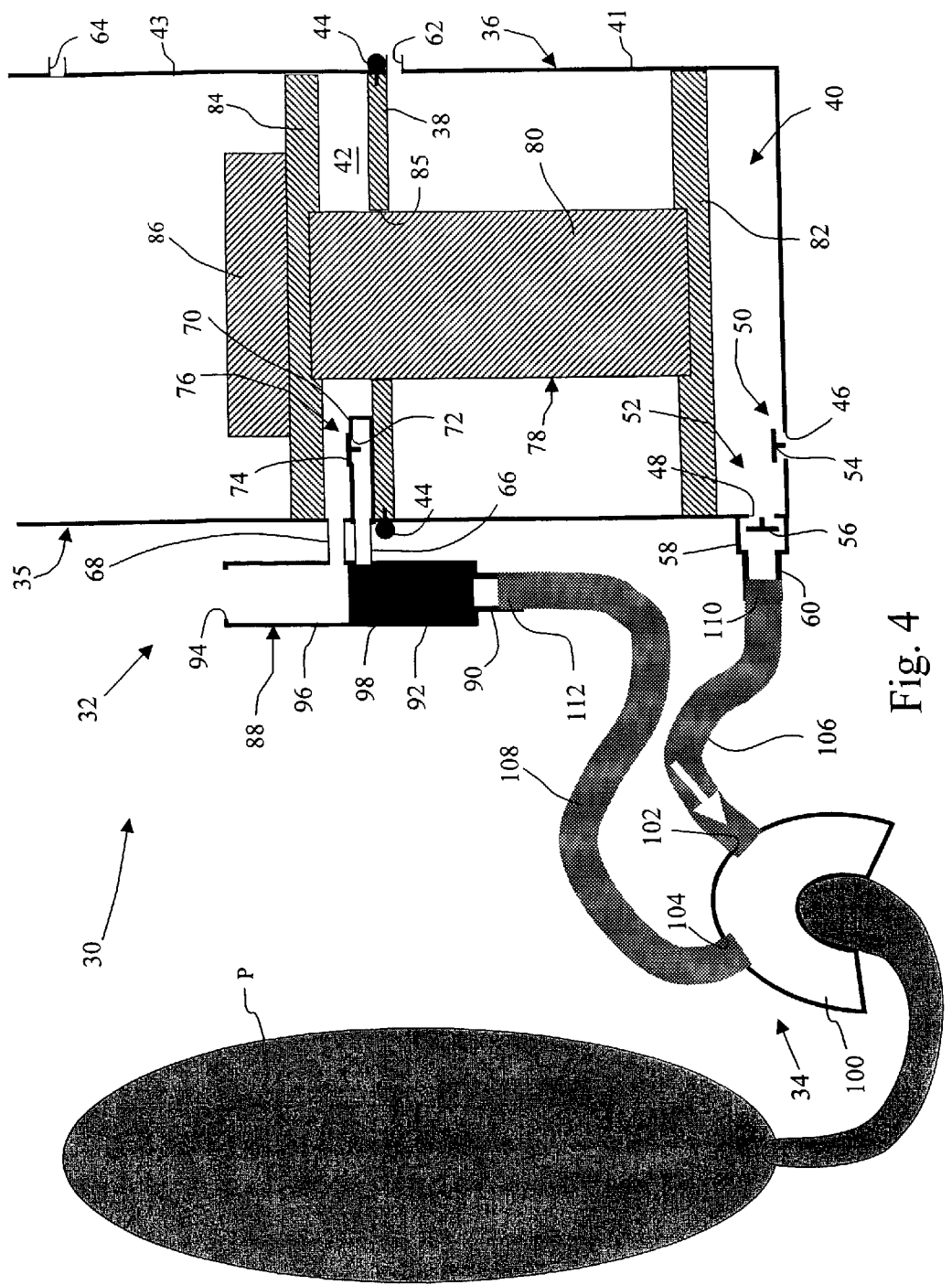
Figure 5:
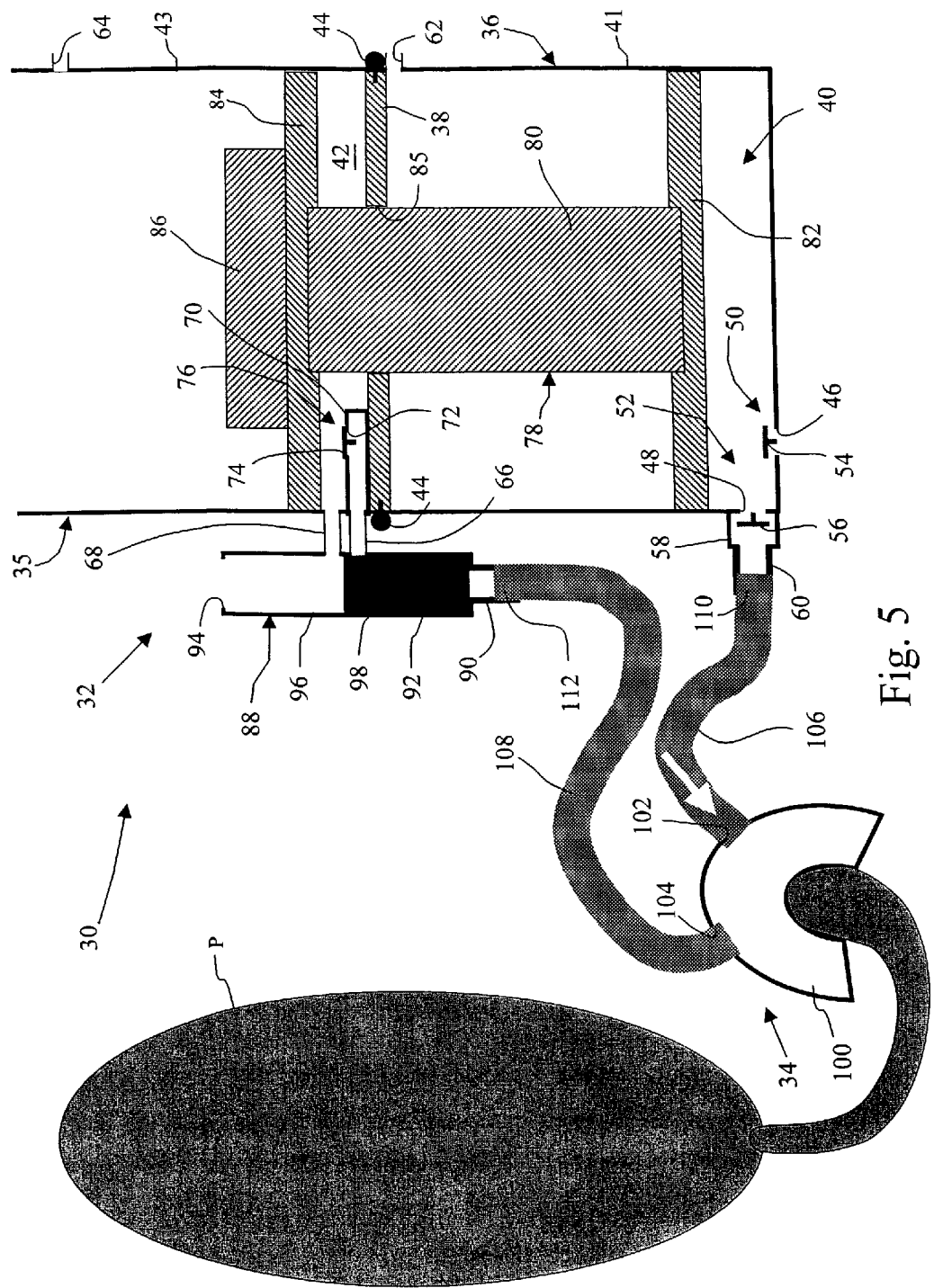
Figure 6:
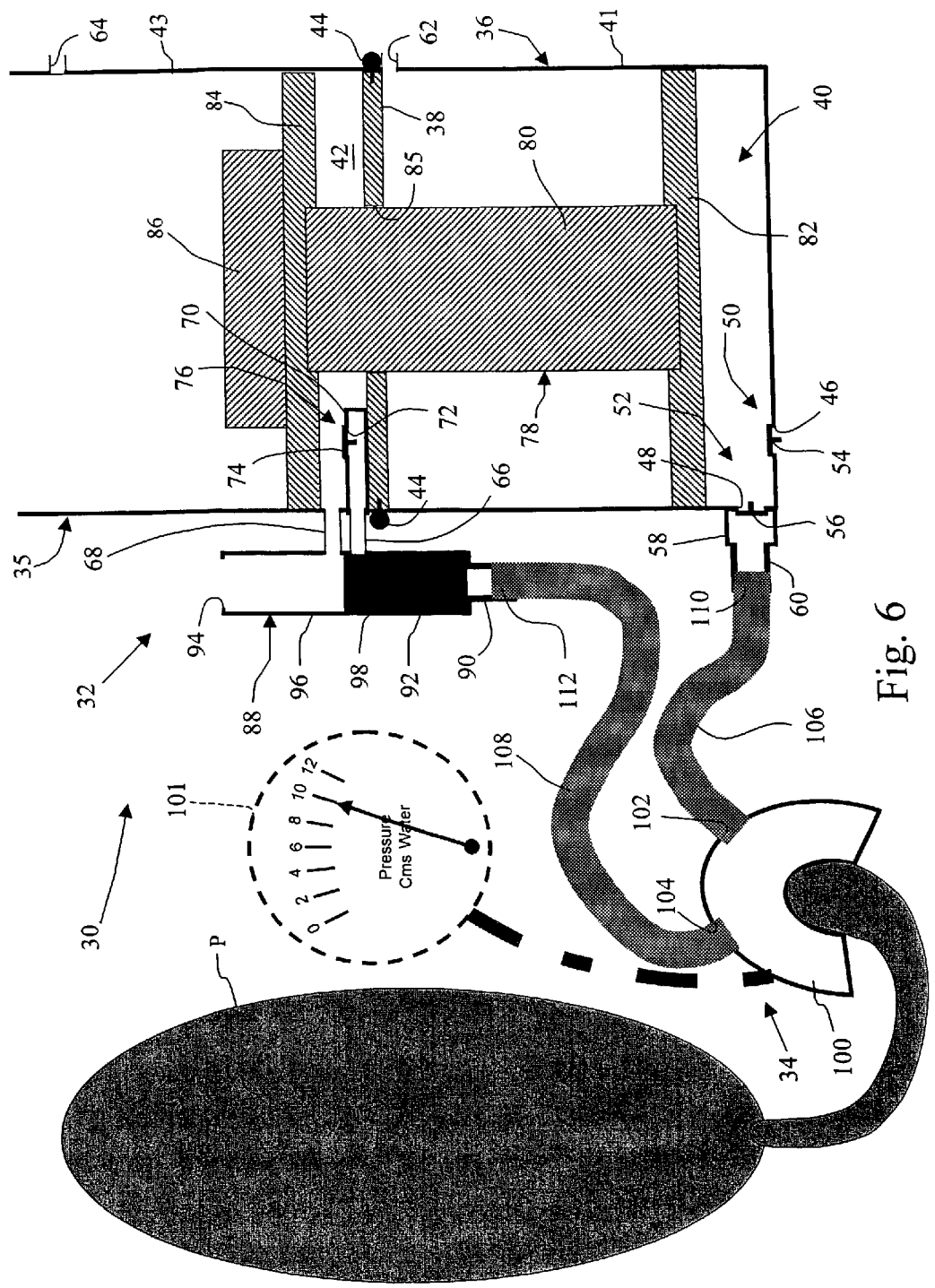

In accordance with an embodiment of the invention, there is provided a device for treating OSA provides a breathable gas supply apparatus that utilizes energy from the patient's exhaled breath to provide assistance for the next inhaled breath.

FIGS. 1-18 show a breathable gas supply apparatus, according to one preferred embodiment of the present invention, in various stages of its operational cycle, to illustrate operational principles thereof. The breathable gas supply apparatus is generally indicated at 30. In the illustrated embodiment, the breathable gas supply apparatus 30 comprises a breathable gas supply system 32 and a respiratory mask assembly 34. The breathable gas supply system 32 is coupled to the respiratory mask assembly 34 and is configured to supply breathable gas through the respiratory mask assembly 34 to the patient.

The breathable gas supply system 32 includes a housing 35 having an outer wall 36 that defines an air chamber 37. The air chamber 37 is divided by an air chamber dividing member 38 to define an inhalation or inspiration chamber 40 in a lower portion 41 of the outer wall 36 and an exhalation chamber 42 in an upper portion 43 of the outer wall 36. The air chamber dividing member 38 is secured to the outer wall 36 on opposite sides thereof by fasteners 44, for example. The fasteners 44 extend through the outer wall 36 and threadedly mount within the dividing member 38. The fasteners 44 may be of any known configuration, such as screws, nails, or nuts and bolts, for example. The dividing member 38 can be secured to the outer wall 36 in other ways as well. For example, an adhesive or bonding material may be applied to the interior surface of the outer wall 36 to bond the dividing member 38 thereto.

The outer wall 36 includes a pair of valve seats 46, 48 (first and second conduits) machined therein. The valve seat 46 is disposed within the inhalation chamber 40 and is configured to receive a sealing structure 54 (a first sealing structure). The valve seat 46 and the sealing structure 54 constitute a first gas supply valve 50. The sealing structure 54 permits fluid communication through the valve seat 46 into the inhalation chamber 40, but prevents breathable gas from leaving the inhalation chamber 40 during patient inhalation, for example.

The valve seat 48 is configured to receive a sealing structure 56 (a second sealing structure). The valve seat 48 and the sealing structure 56 constitute a second gas supply valve 52. The sealing structure 56 permits fluid communication through the valve seat 48, but prevents breathable gas from leaving the inhalation chamber 40 during patient exhalation, for example. The gas supply valve 50 is disposed within an inspiration valve housing 58.

The inspiration valve housing 58 is attached to the outer wall 36 in fluid communication with the valve seat 48 and includes an outlet 60 formed therein. The outlet 60 has a substantially smaller transverse cross section than the housing 58, which is configured to receive a portion of the mask assembly 34.

An air passageway 62 is formed in the outer wall 36 on the opposite side of the inhalation chamber 40. The air passageway 62 permits air passage through the outer wall 36 during the operation of the breathable gas supply apparatus 30, as will be described in further detail below.

In the exhalation chamber 42, an air passageway 64 is formed in the outer wall 36. The air passageway 64 is substantially similar in construction as the air passageway 62 in that it permits air passage through the outer wall 36 during the operation of the breathable gas supply apparatus 30, as will be described in further detail below. On the opposite side thereof (left side in FIG. 1), an exhalation inlet 66 and a gas washout vent 68 extend from the outer wall 36 in fluid communication with the exhalation chamber 42. An exhalation valve housing 70 is positioned in fluid communication with the exhalation inlet 66. The exhalation valve housing 70 extends inwardly from the outer wall 36 and into the exhalation chamber 42 so as to be positioned adjacent to the upper surface of the dividing member 38. The exhalation valve housing 70 forms a valve seat 72 (a third conduit), which is configured to receive a sealing structure 74 (a third sealing structure). The sealing structure 74 permits fluid communication through the valve seat 72 into the exhalation chamber 42, but prevents exhaled gas to exit the exhalation chamber 42 by escaping from the inlet 66 during patient inhalation, for example. The valve seat 72 and the sealing structure 74 constitute an exhalation valve 76.

A movable structure 78 (FIG. 1) is in the form of a piston-like member that is disposed within the inhalation and exhalation chambers 40, 42. The piston 78 has a body portion 80 interposed between a lower end portion 82 and an upper end portion 84. The body portion 80 has a generally tubular configuration and extends through a central opening 85 in the air chamber dividing member 38 so as to be slidably received within the opening 85. The body portion 80 moves along the opening 85 when the movable structure 78 moves in phase with a respiratory cycle of the patient, as will be described in greater detail below.

Each end portion 82, 84 has a groove (not shown) that is configured to receive an opposite end of the body portion 80 and may be secured thereto by fasteners, adhesive, bonding material or some other securing means known in the art, for example. The lower end portion 82 of the piston 78 is disposed within the inhalation chamber 40 while the upper end portion 84 thereof is disposed within the exhalation chamber 42. Seals, such as piston rings, for example, may be positioned between the lower and upper ends 82, 84 of the piston 78 and the outer wall 36 of the housing 35 to provide an effective seal between the inhalation chamber 40 and the exhalation chamber 42.

A weight 86 is secured to the upper end portion 84 of the pressure applying piston 78. The weight 86 may be of any configuration, however, the weight 86 may be configured to cooperate with the piston 78 to provide 12 cms water pressure in the exhalation chamber 42 and 10 cms water pressure in the inhalation chamber 40, for example. The provided pressures of 10 and 12 cms water pressure are determined by the weight of the piston 78 and the weight 86 divided by the respective area of each chamber 40, 42. The value of 10 cms water pressure is the treatment pressure, i.e. the pressure supplied to the patient on inspiration, and is indicative of an illustrative example. The piston 78 can provide any suitable pressure value, for example, a pressure value within a range of 2-20 cms water pressure.

The pressure value provided by the piston 78 is based on the formula P=F/A, wherein P is a pressure value (either for inhalation or exhalation), F is a force value (expressed in weight of the piston assembly, e.g., the piston 78 and the weight 86) and A is an area value (i.e., the cross-sectional area of the piston 78 or portions thereof, for example). During operation, the formula P=F/A can be applied to both the exhalation chamber 42 and the inhalation chamber 40, which, for example, can be expressed as $P_{exhalation}=F_{exhalation}/A_{exhalation}$ and $P_{inhalation}=F_{inhalation}/A_{inhalation}$. The area value $A_{exhalation}$ in the exhalation chamber 42 can be calculated by subtracting the cross-sectional area of the body portion 80 of the piston 78 from the cross-sectional area of the upper end portion 84, thus creating a pressure value $P_{exhalation}$. In the inhalation chamber, the area value $A_{inhalation}$ can be calculated by the cross-sectional area of the lower end portion 82 of the piston 78, which is larger than the area value $A_{exhalation}$ thus creating a pressure value $P_{inhalation}$. During patient exhalation, for example, the piston 78 will rise because the pressure in the exhalation chamber 42 ($P_{exhalation}$) is greater than the pressure in the inhalation chamber 40 ($P_{inhalation}$).

A valve or tube 88 having a substantially hollow configuration is coupled to the outer wall 36 in fluid communication with the exhalation chamber 42 through the inlet 66 and the vent 68. The valve 88 has a narrowed end 90 disposed on a lower portion 92 thereof. The narrowed end 90 is configured to receive a portion of the mask assembly 34, as will be described in further detail below. The valve 88 defines an opening 94 on the upper open-ended portion 96 thereof. The gas washout vent 68 is configured to release exhaled gas, such as carbon dioxide, into the atmosphere through the opening 94.

Disposed within the valve 88 is another movable structure in the form of an air directing member 98, which is slidably movable between a first position and a second position thereof. In the first position thereof, the air directing member 98 is slidably moved into the lower portion 92 of the valve 88 where it directs exhaled gas to flow through the gas washout vent 68 and out the opening 94 by sealing the exhalation inlet 66. In the second position thereof, the air directing member 98 is slidably moved into the upper portion 96 of the valve 88 where it directs exhaled gas to flow through the exhalation inlet 66 by sealing the gas washout vent 68.

The housing 35, the piston 78 and the air directing member 98 can have any cross-sectional shape, such as complementing rectangular or round cross-sectional portions. Although the housing 35, the piston 78 and the air directing member 98 can be formed to be any dimensions or size, the housing 35 might have a height of 10-15 centimeters, an inner diameter of 10-15 centimeters and a volume of 0.75-1.5 liters, for example.

The air directing member 98 and the piston 78 constitute a pressure actuator assembly of the apparatus 30. The air directing member 98 may be any configuration, but is illustrated as a weight capable of providing 11 cms water pressure, for example, which is determined by the weight of the air directing member 98 divided by its area. The value of 11 cms water pressure is the pressure needed to raise the air directing member 98 and is indicative of an illustrative example. The air directing member 98 can be any weight capable of providing a suitable pressure value, for example, a pressure value within a range of 2-20 cms water pressure. Conceptually, the pressure only needs to be set between the respective pressures of the inhalation chamber 40 and the exhalation chamber 42. Although the apparatus is more stable when the pressure is set between the respective pressures of the inhalation chamber 40 and the exhalation chamber 42, the initial pressure needed to raise the air directing member 98 could be the same as the pressure needed to raise the piston 78.

The respiratory mask assembly 34 includes a respiratory mask 100 having an inspiration port 102 and an exhalation port 104 formed therein. The respiratory mask 100 may embrace the nose, mouth or full face (combination nose and mouth) of the patient and is preferably suitably constructed for the administration of CPAP treatment. The mask 100 may be used in treating sleep disordered breathing (SDB), for example. Furthermore, the respiratory mask 100 may include nasal prongs (cannulae) that are inserted into the nostrils of a patient at the entrance to the airway. The respiratory mask 100 may include retaining straps or harnesses in order to prevent air leakage when firmly secured to the patient.

A flexible conduit 106 extends from the inspiration port 102 of the respiratory mask 100 and a flexible conduit 108 extends from the exhalation port 104 of the respiratory mask 100. The flexible conduits 106, 108 can be integrally formed with the ports 102, 104, respectively, or may also be secured thereto by adhesive or other known securing means, such as clamps.

An end 110 of the conduit 106 is removably connected, such as, for example, by friction fit, to the tube receiving outlet 60 of the inspiration valve housing 58 so as to allow air passage from the inhalation chamber 40 through the valve 52 and into the respiratory mask 100. An end 112 of the conduit 108 is removably connected, such as, for example, by friction fit, to the narrowed end 90 of the valve 88 so as to allow air passage from the respiratory mask 100 through the exhalation valve 76 into the exhalation chamber 42.

In an embodiment not shown, the gas washout vent 68 may be incorporated within the respiratory mask 100 so to encourage a circulation of flow within the respiratory mask 100 and so as to eliminate exhaled carbon dioxide gas therethrough and encourage the inspiration of the supplied breathable gas from the inhalation chamber 40. Further, by locating the gas washout vent 68 in close proximity to the respiratory mask 100, the venting efficiency is increased and the overall gas outflow is minimized, thereby reducing the opportunity for noise reduction during operation of the breathable gas supply apparatus 30.

Alternatively, the air supply valve 52 could be incorporated into mask 100, wherein the air supply valve 52 would permit breathable gas to flow into the mask 100 from the inhalation chamber 40, but would prevent the breathable gas to exit the mask 100.

Now, reference is made to FIGS. 1-18, which illustrate the operation of the breathable gas supply apparatus 30 when positioned in communication with a spontaneously breathing patient. A patient's lungs P are shown schematically, whereby the respiratory mask 100 is firmly secured over their nose, mouth, or face as described above. Motions of the patient's lungs, as well as motions of the movable parts of the apparatus 30 are illustrated in subsequent positions during operation thereof. In FIGS. 2, 6-7, 13, 14 and 17, a pressure measuring device 101 is shown in phantom to illustrate various pressure changes experienced by the patient wearing mask 100 during the operation of the apparatus 30.

FIG. 1 shows the apparatus 30 in an initial position. The valves 50, 52 and 76 are closed so as to prevent air passage therethrough and the piston 78 is positioned in its gas supplying position wherein the upper end portion 84 is slightly spaced above the gas washout vent 68. The air directing member 98 is disposed at the lower portion 92 of the valve 88 in its first position. When the apparatus 30 is in this initial position, and a patient inhales, for example, the valves 50, 52 can be opened to allow the patient to inhale breathable air from the atmosphere. In this case, the inhalation of the patient would open the valve 52. A change in pressure in the inhalation chamber 40 would be produced, which would cause valve 50 to open to allow breathable air into the inhalation chamber 40 and to the patient through valve 52 from the atmosphere.

FIGS. 2-6 are sequential views of the breathable gas supply apparatus 30 illustrating the patient's lungs P inflating as the patient inhales a supply of breathable gas, such as oxygen, from the atmosphere. As a patient begins to inhale, the air supply valves 50, 52 open to allow air passage therethrough and the patient may draw breathable air from the atmosphere into the mask 100 through the air supply valves 50, 52, flexible conduit 106 and inhalation port 102. The supply of breathable gas enters the patient's lungs P until patient inhalation stops.

Figure 7:
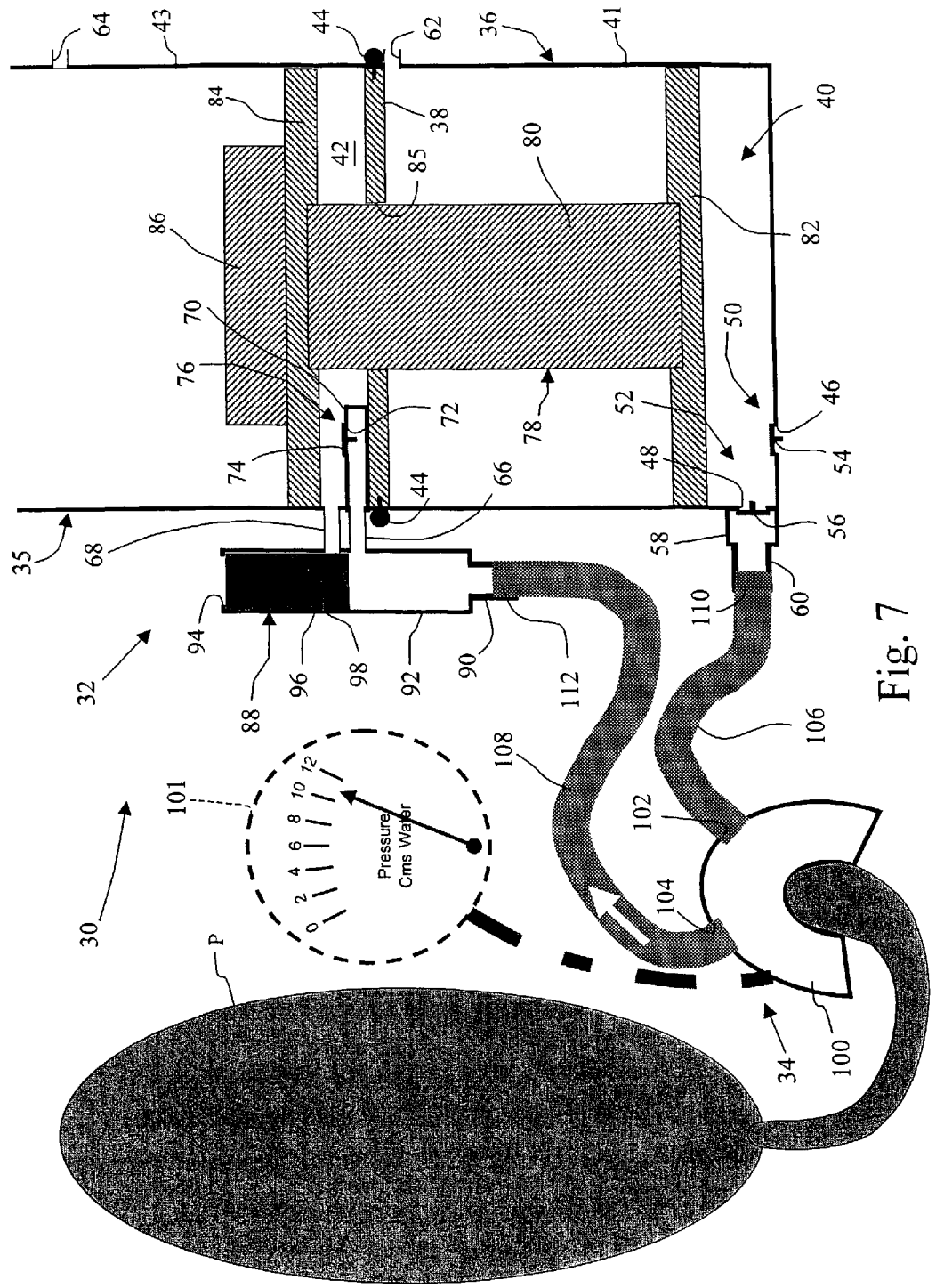
FIGS. 7-13 are schematic views of the breathable gas supply apparatus shown in FIG. 1 during subsequent exhalation positions thereof, wherein the patient is exhaling and the patient's exhaled carbon dioxide moves the second movable structure into its first position, then travels through the third conduit to move the first movable structure into its first position, to thereby supply breathable gas through the first conduit and into the inhalation chamber.

At the beginning of exhalation as shown in FIG. 7, the valves 50, 52 close to prevent breathable gas from passing therethrough.

Figure 8:
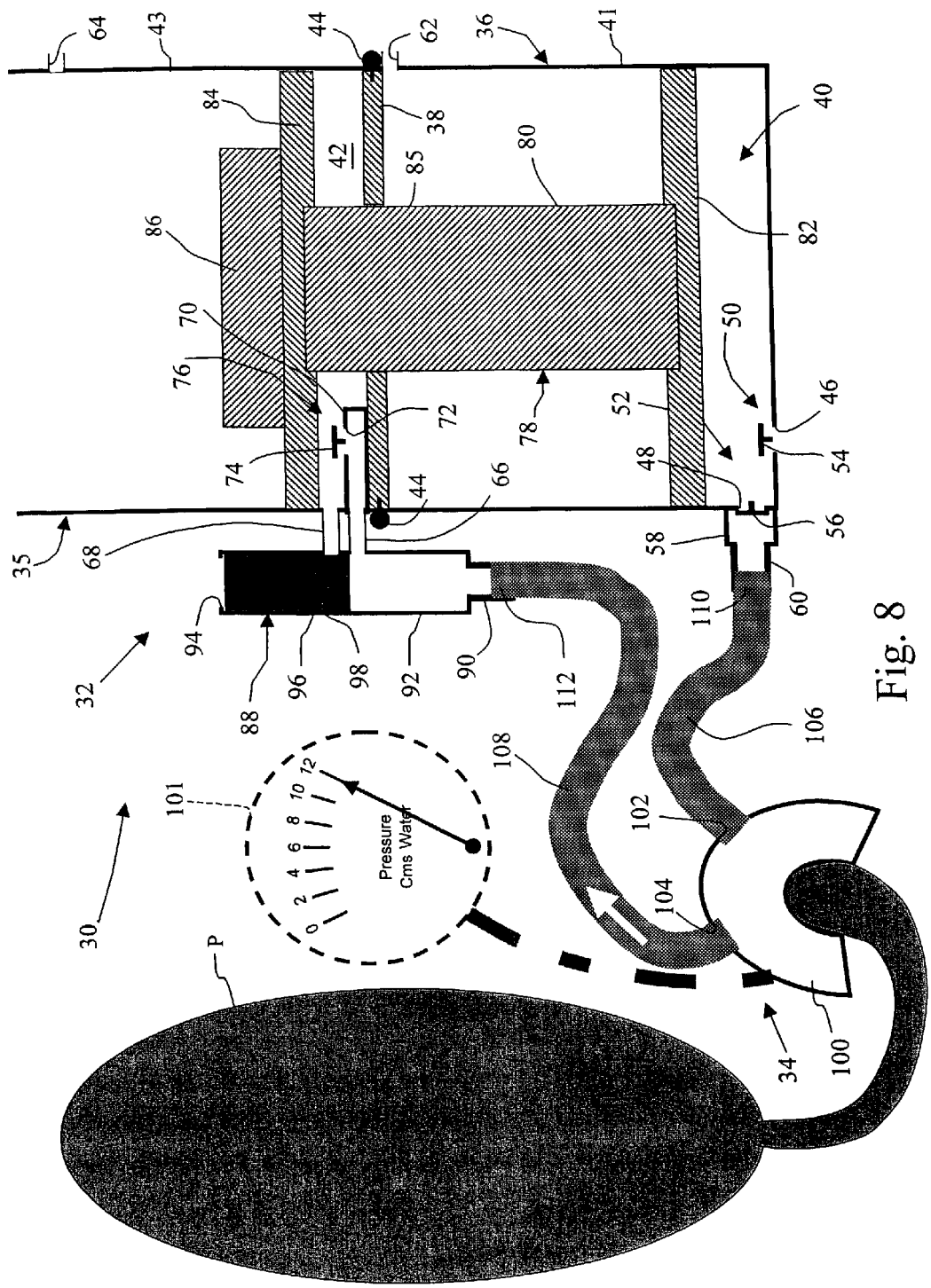
Figure 9:
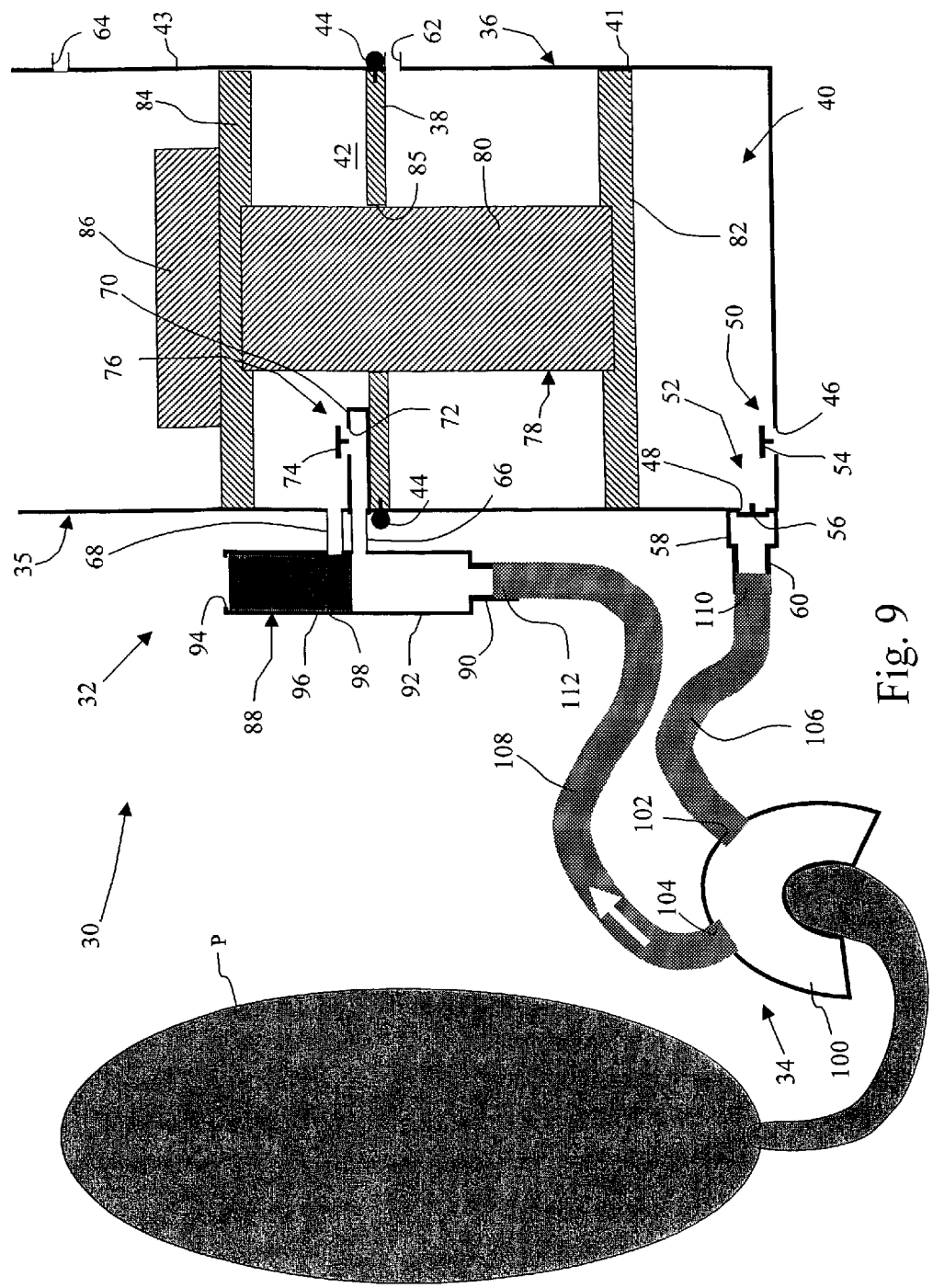
Figure 10:
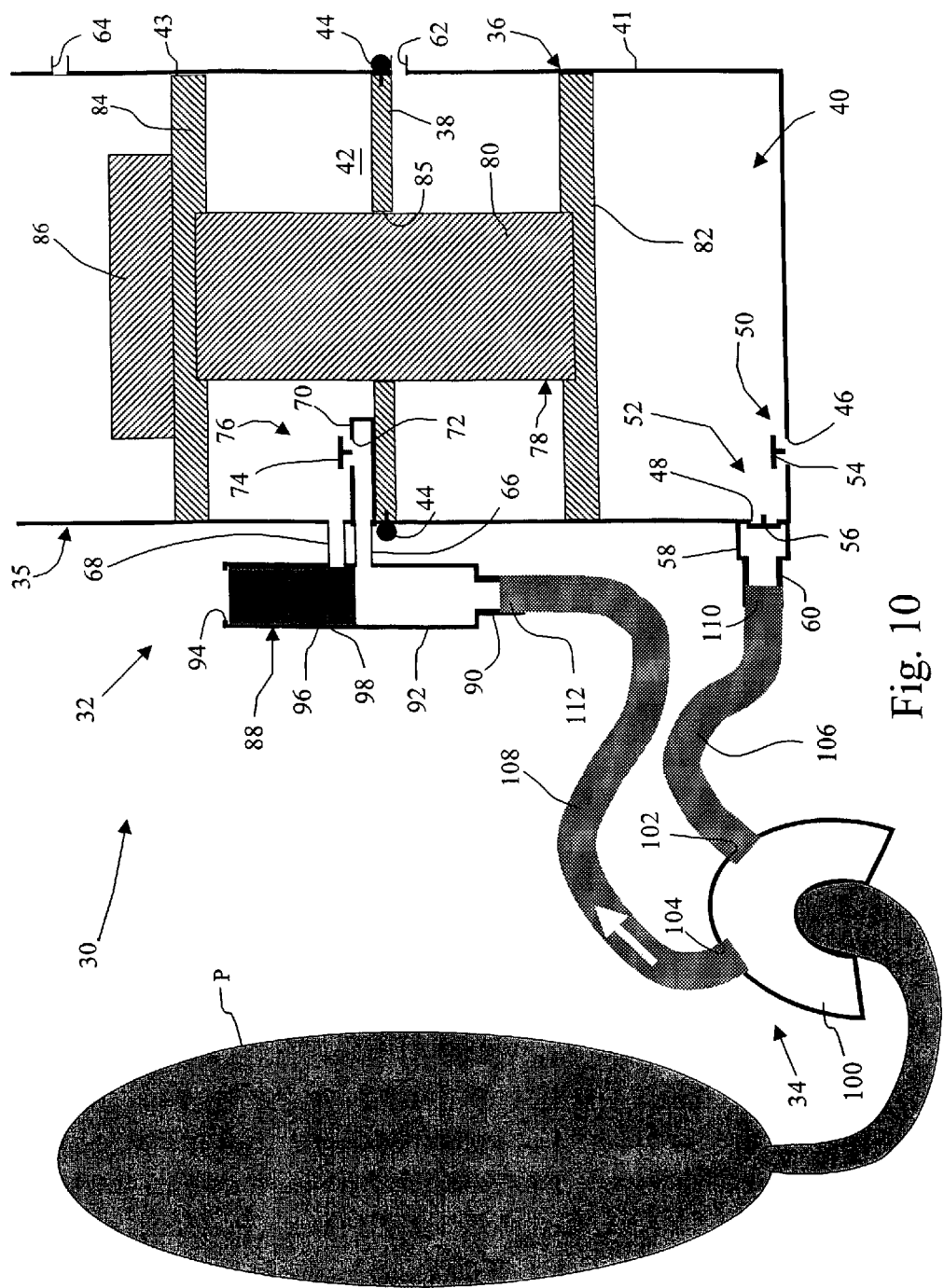
Figure 11:
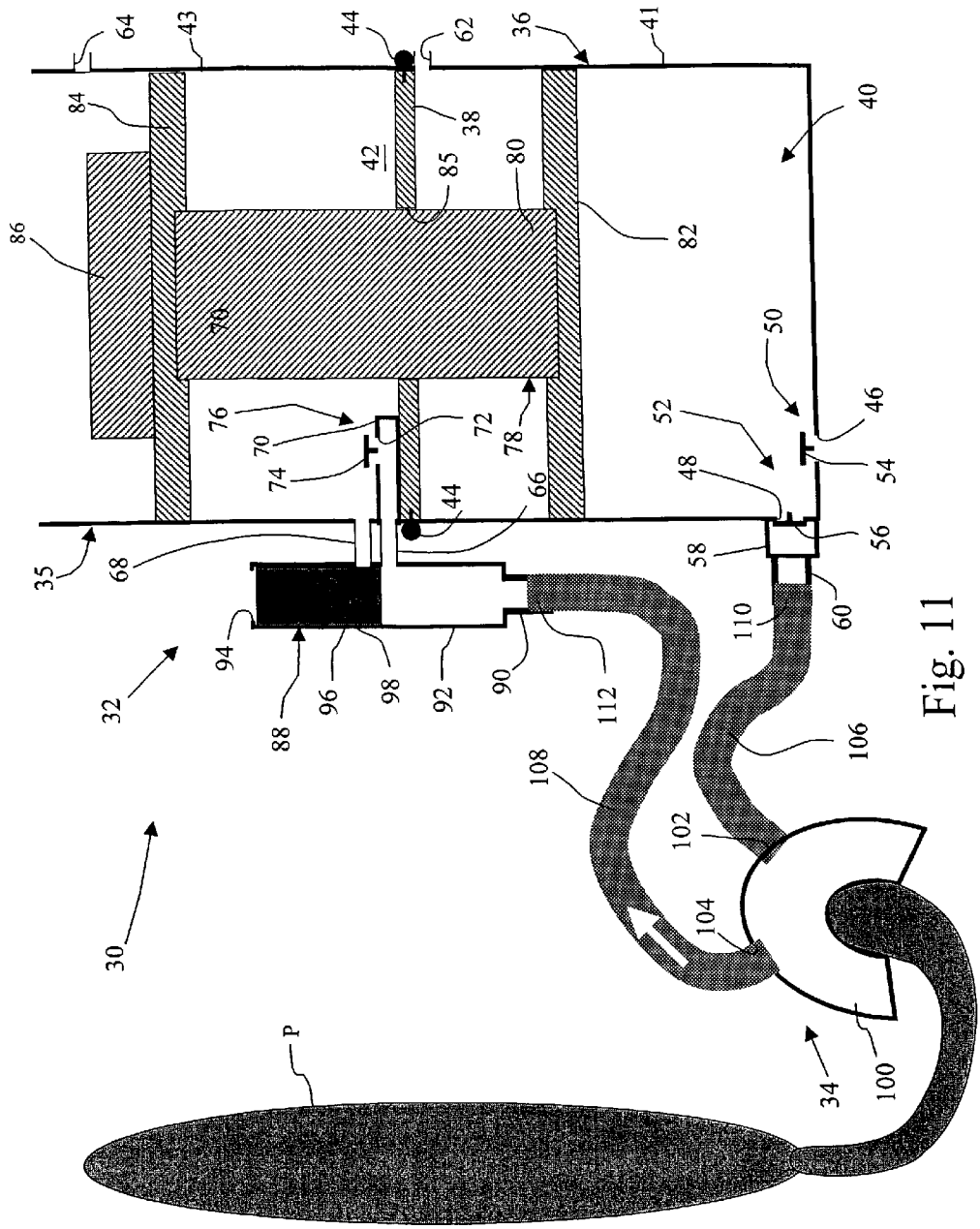
Figure 12:
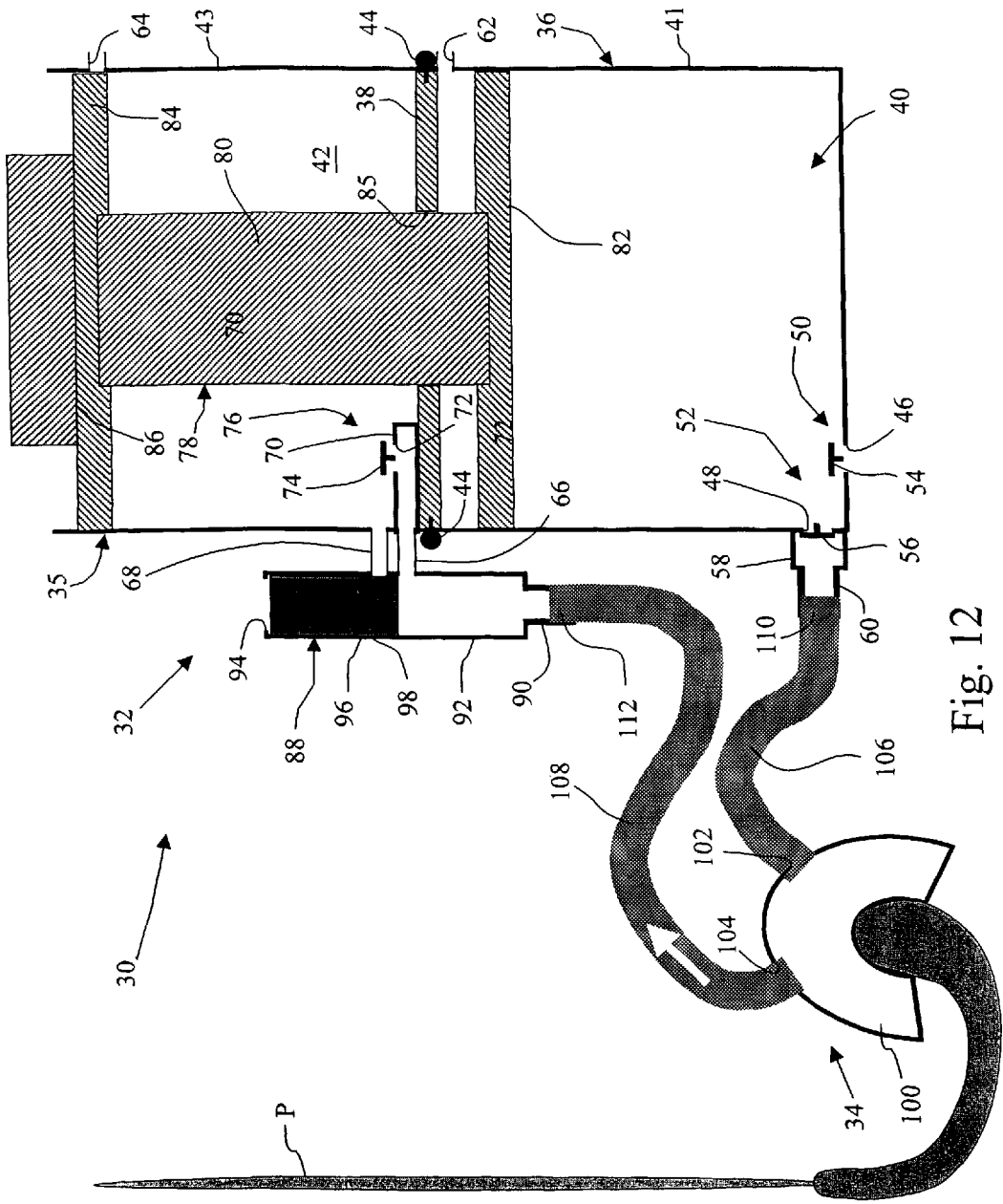
Figure 13:
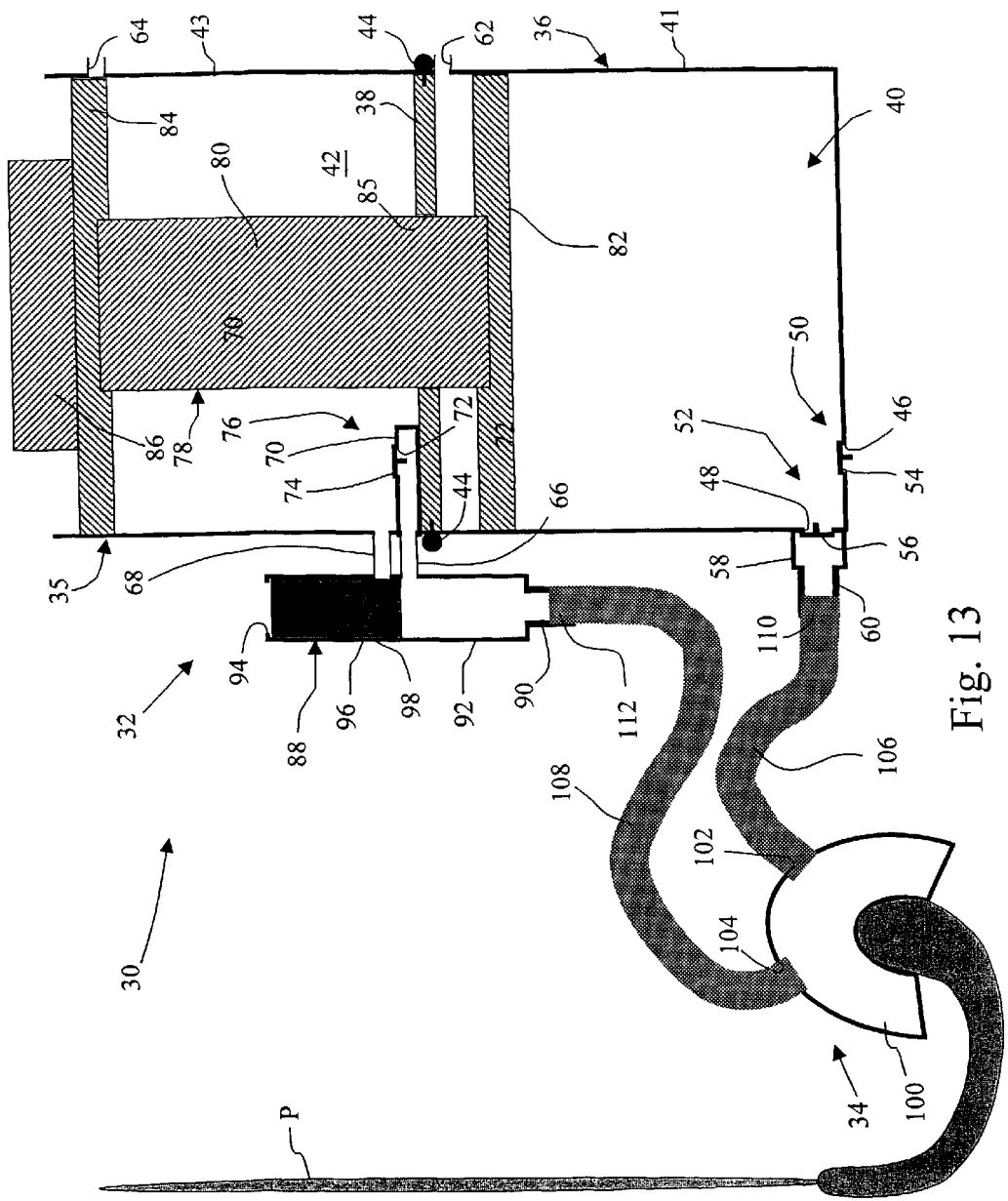
Figure 14:
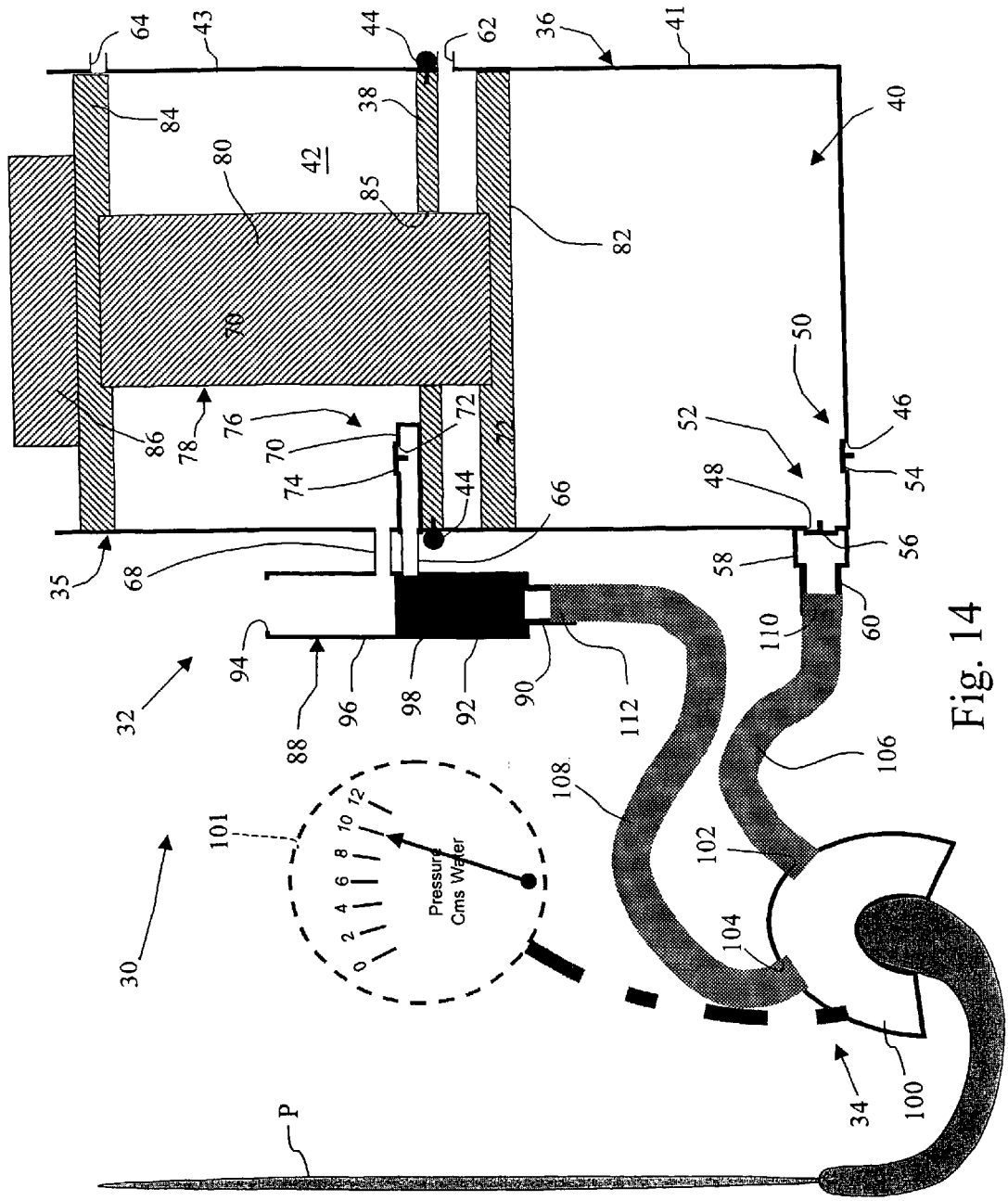
FIGS. 14-18 are schematic views of the breathable gas supply apparatus shown in FIG. 1 during subsequent inhalation positions thereof. As illustrated, first and second movable structures move toward second positions thereof to thereby facilitate carbon dioxide being supplied through the gas washout vent into the atmosphere and breathable gas being supplied from the inhalation chamber through the second conduit to the respiratory mask, thus enabling the patient to inhale the breathable gas supplied from the inhalation chamber.

As the patient exhales, as shown in FIGS. 7 and 8, exhaled gas, such as carbon dioxide, is prevented from flowing through the port 102 and the conduit 106 by the air supply valve 52. The breathable gas flows out of the port 104 and through the conduit 108. The pressure within the mask 100 increases until the pressure reaches a certain level. The pressure level for moving the air directing member 98 may be, for example, 11 cms water pressure. When the pressure reaches the certain pressure level, for example, as shown in FIG. 7, the air directing member 98 moves to its second position. In its second position, the air directing member 98 directs the exhaled gas to flow through the exhalation inlet 66 and the exhalation valve 76 so that exhaled gas begins to fill the exhalation chamber 42.

As exhalation continues, the pressure within the exhalation chamber 42 continues to increase until the pressure exceeds the weight of the piston 78 and the weight 86. When the pressure multiplied by the area reaches an amount substantially equal to the weight of the piston 78 and the weight of the weight 86, for example, the piston 78 begins to move toward its second position. As the piston 78 moves into its second position thereof, the passageways 62, 64 allow gas passage therethrough. The pressure within the apparatus 30 draws the air supply valve 50 into its open position such that a supply of fresh breathable gas is drawn therethrough into the inhalation chamber 40.

During exhalation of the patient, the piston 78 moves against the force of gravity and the weight 86 from its gas supplying position (FIG. 1), where the upper end portion 84 is slightly spaced from the gas washout vent 68 to its gas receiving position (FIGS. 12, 13, 14 and 15) where the upper end portion 84 is adjacent to the air passageway 64. The extent of upward movement of the upper end portion 84 of the piston 78 will vary depending on the patient's breath. During exhalation, mechanical work done by the patient is stored in the form of potential energy, as the piston 78 moves upwardly.

When exhalation ceases, the piston 78 is disposed in its $2^{nd}$ position in which the upper end portion 84 may be adjacent to the passageway 64 and the air directing member 98 moves to its first position to allow exhaled gas to escape to atmosphere. Fresh breathable gas is continuously drawn into the inhalation chamber 40 until the piston 78 reaches the $2^{nd}$ position. When inhalation begins, the valves 50 and 76 close to prevent gas from flowing therethrough and so that the inhalation chamber 40 can maintain a supply of fresh breathable gas therein. During inhalation, the patient utilizes only stored mechanical energy which is then transferred to the patient by the piston 78 to assist the patient's respiratory effort as the piston 78 moves downwardly.

FIGS. 14-18 show the patient beginning to inhale the supply of breathable gas within the inhalation chamber 40 through the valve 52 and into the mask 100. The patient's inhalation causes valve 52 to open in order to permit the supply of breathable gas to enter the mask 100 therethrough. The pressure within the respiratory mask 100 and the flexible conduits 106, 108 decreases to 10 cms water pressure, for example, which is determined by the weight of the piston 78 divided by its area. This pressure value may be altered based on the size of the piston 78, for example.

If the patient continues to inhale after inhaling the entire supply of breathable gas in the inhalation chamber 40 (i.e., the patient needs more air than accumulated in the inhalation chamber 40), the valves 50, 52 can be opened to allow the patient to inhale additional breathable air from the atmosphere. In this case, the inhalation of the patient would open the valve 52. A change in pressure in the inhalation chamber 40 would be produced, which would cause valve 50 to open to allow breathable air into the inhalation chamber 40 and to the patient through valve 52 from the atmosphere.

Figure 15:
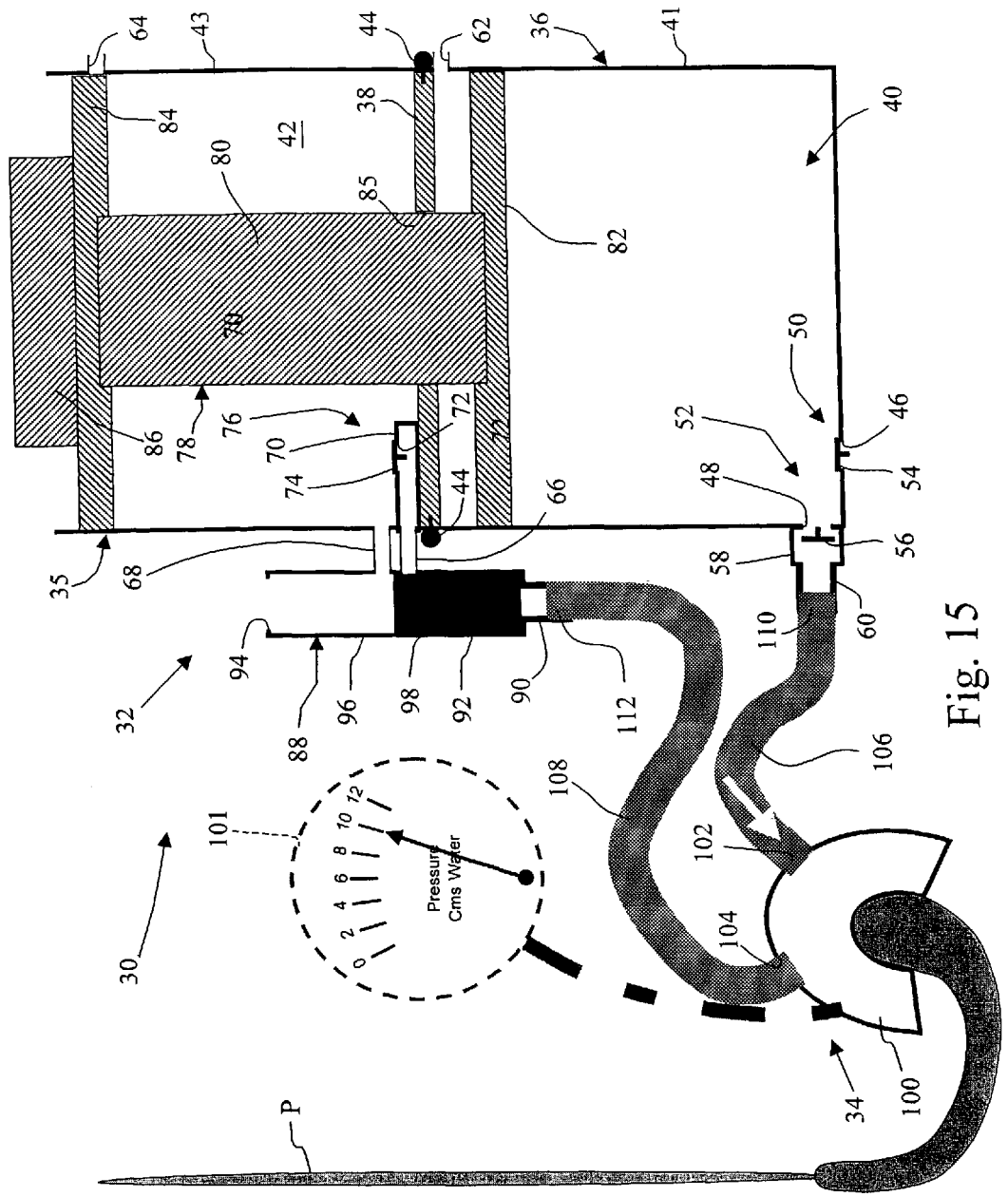
Figure 16:
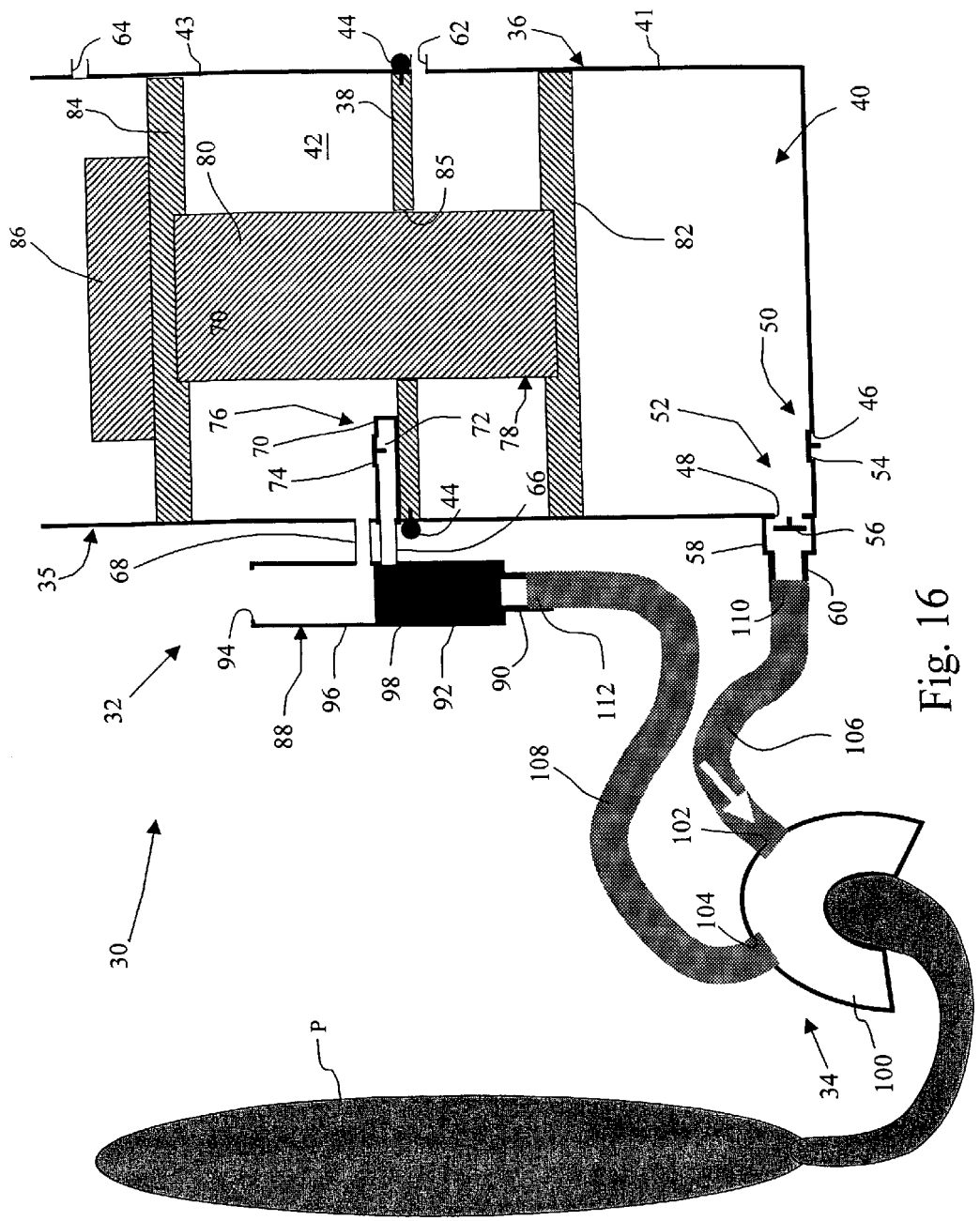
Figure 17:
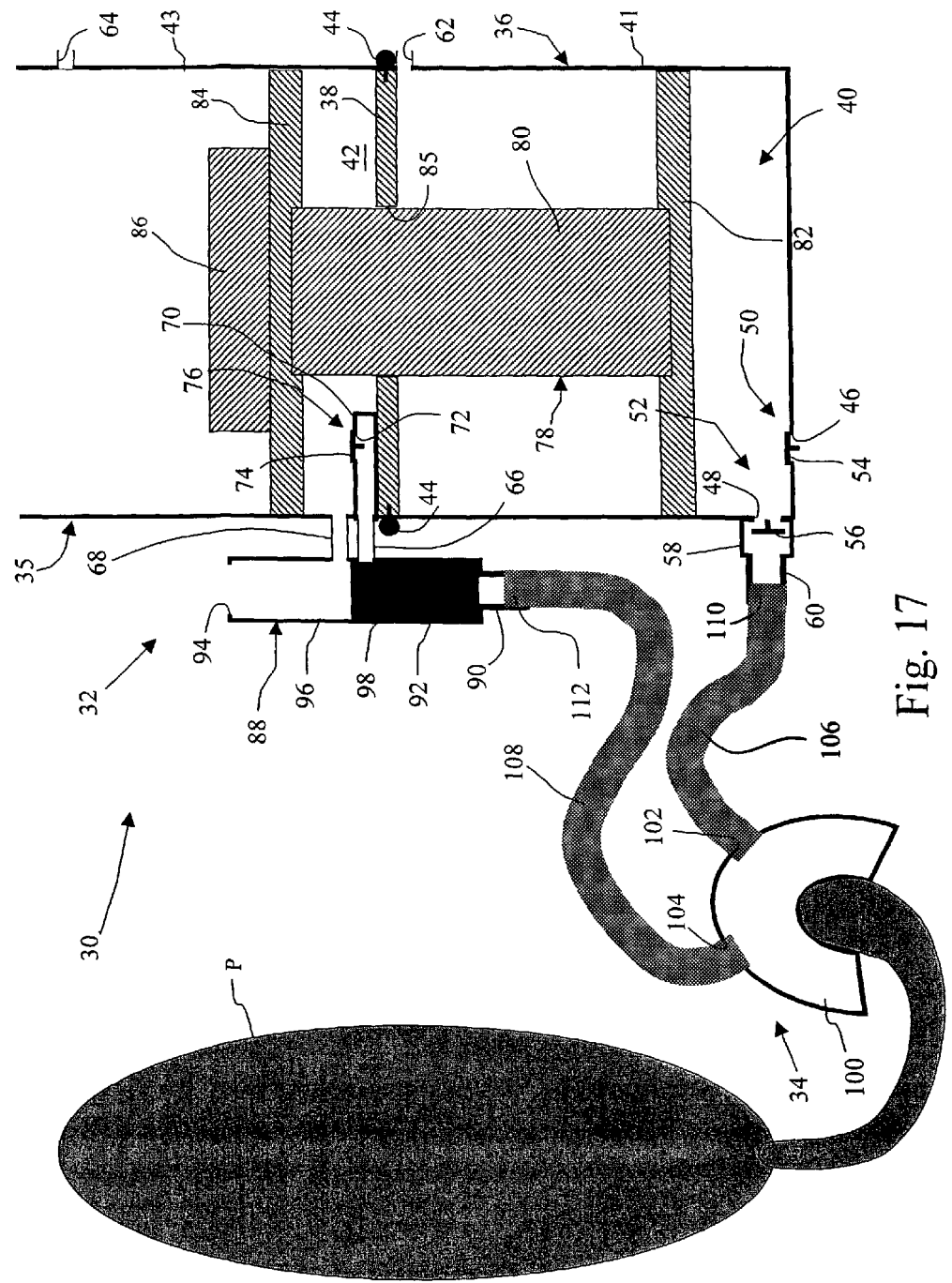
Figure 18:
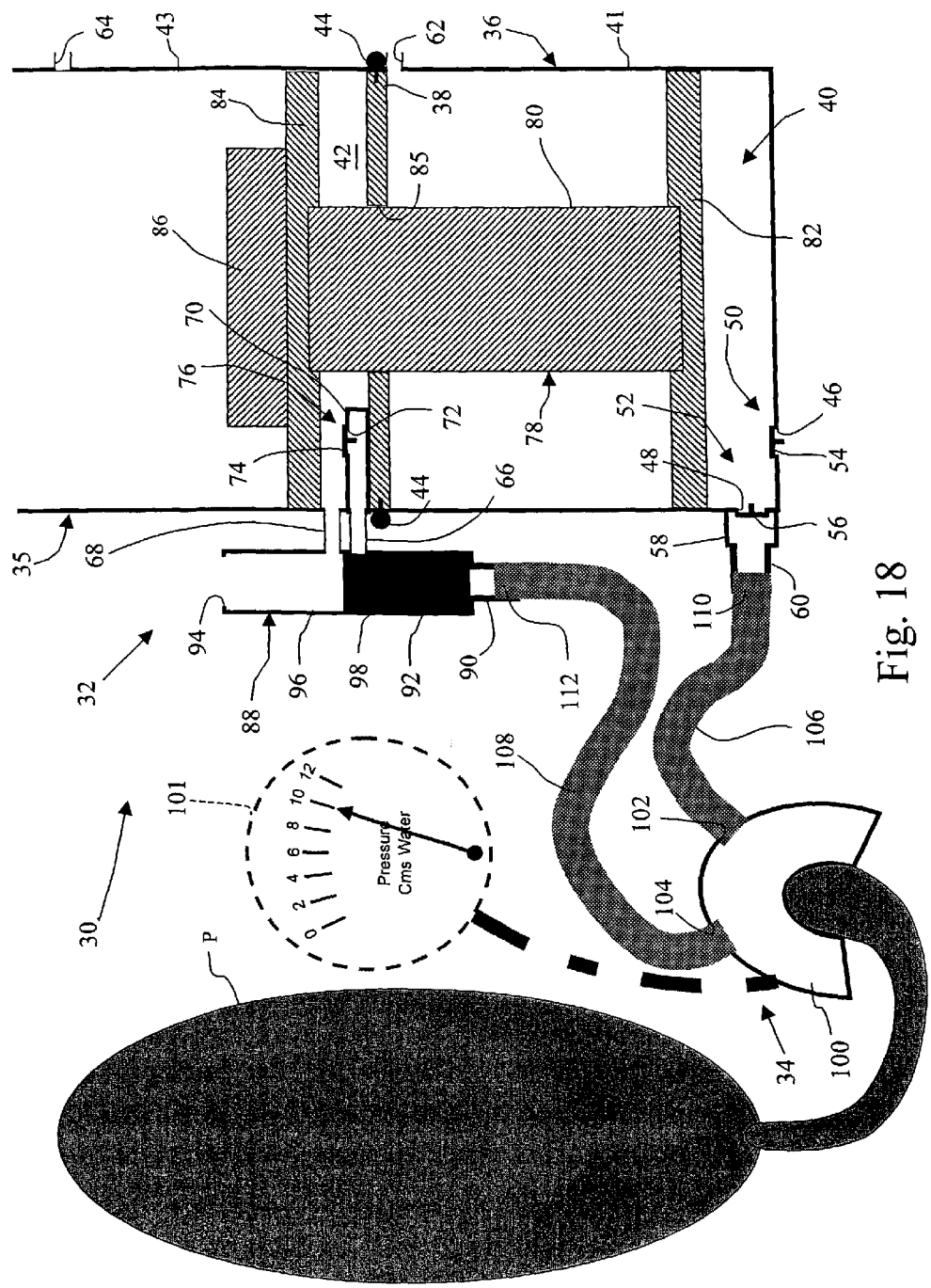

With the pressure decrease to less than 11 cms water pressure, the force of gravity and the weight of the air directing member 98 facilitate movement of the air directing member 98 into the first position thereof, as shown in FIG. 15, where it directs exhaled gas from the exhalation chamber 42 to flow through the gas washout vent 68. The weight 86 and the force of gravity move the piston 78 toward its first position. As a result, the upper portion 84 of the piston 78 forces exhaled carbon dioxide out of the exhalation chamber 42 through the gas washout vent 68, valve 88, opening 94 and into the atmosphere. The lower portion 82 of the piston 78 directs the supply of breathable gas collected within the inhalation chamber 40 through the air supply valve 512, the conduit 106, inhalation port 102 and into the mask 100 to assist patient inhalation.

During inhalation of the patient, the force of gravity in combination with the weight 86 move the upper end portion 84 of the piston 78 from a position where it is slightly spaced from the air passageway 64 (FIGS. 12-15) to a position where it is slightly spaced from the gas washout vent 68 (FIG. 1).

As the patient continues respiration, i.e., breathing by taking subsequent breaths, the apparatus 30 will continuously operate as described above, specifically in accordance with FIGS. 7-18, which constitute one full breath (inhalation and exhalation) of the patient. FIGS. 14-18 constitute the inhalation half of the patient's breath and FIGS. 7-13 constitute the exhalation half of the patient's breath. However, when the mask 100 is removed from the patient or if the patient stops exhaling, the apparatus 30 will return to its initial position shown in FIG. 1, which may be utilized when storing the apparatus 30, for example.

Conceptually, the illustrative pressures described above with reference to the apparatus 30 can be set within the range of 2-20 cms water pressure, for example. The pressure needed to raise the air directing member 98 depends on the exhalation pressure, i.e., the pressure at which the patient exhales. For example, the apparatus 30 has an exhalation pressure and a treatment pressure, which is lower than the exhalation pressure. The pressure difference between the treatment pressure and the exhalation pressure is sufficient so that the air directing member 98 can successfully operate at a pressure set between the exhalation pressure and the treatment pressure.

FIGS. 19-23 show a breathable gas supply apparatus 130 for a patient, which is another embodiment of the breathable gas supply apparatus 30. In the following description of the embodiment illustrated in FIGS. 19-23, only the points of difference of the embodiment from the embodiment illustrated in FIGS. 1-18 will be described. That is, in those embodiments, the constituent parts the same as those in the first embodiment are referenced correspondingly in the drawings and the description about them will be omitted. The breathable gas supply apparatus 130 operates in substantially the same manner as the breathable gas supply apparatus 30, but realizes a more simplified construction.

The breathable gas supply apparatus 130 comprises a housing 131 and a respiratory mask assembly 34, which is the same respiratory mask assembly illustrated in FIG. 1. The housing 131 is coupled to the respiratory mask assembly 34 and is configured to supply breathable gas through the respiratory mask assembly 34 to the patient and to remove exhaled gas from the patient through the respiratory mask assembly 34, as will be described in greater detail below. The respiratory mask assembly 34 can be connected to the valve 88 and the air directing member 98 in a manner similar as that described above with respect to the apparatus 30 shown in FIG. 1.

The housing 131 has an upper member 132 and a lower member 134 in fluid communication with one another so that the upper member 132 can move with respect to the lower member 134. The upper member 132 and the lower member 134 can be in the form of concentric cylinders or may be configured to have any other complementing configuration. Although the upper member 132 and the lower member 134 can be formed to be any dimensions or size, the upper member 132 and the lower member 134 might have a height of 10-15 centimeters, an inner diameter of 10-15 centimeters and a volume of 0.75-1.5 liters, if in the form of concentric cylinders.

Figure 19:
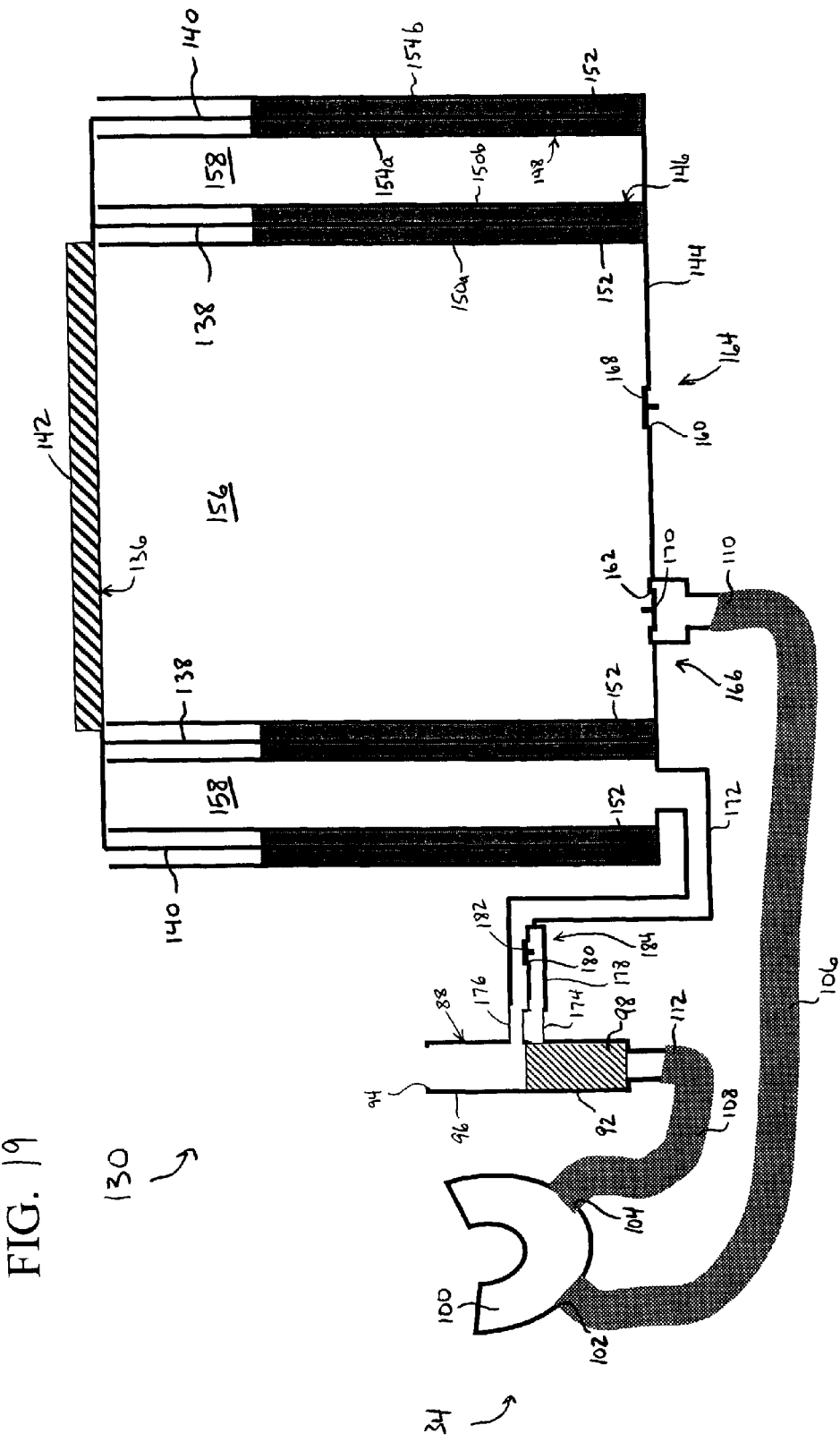
FIG. 19 is a schematic view of a breathable gas supply apparatus in an initial position thereof according to another embodiment of the present invention.

As shown in FIG. 19, the upper member 132 includes an upper wall 136 having an inner wall 138 and an outer wall 140 downwardly extending therefrom. The inner wall 138 and the outer wall 140 extend substantially parallel with one another. A weight 142 can form a portion of the upper wall 136 (shown positioned between the inner wall 138 of the upper member 132 in FIG. 19), for example, or can be fixedly attached to the upper wall 136 by a fastener, bonding material or adhesive.

The lower member 134 includes a lower wall 144 having an inner wall structure 146 and an outer wall structure 148 upwardly extending therefrom. The inner wall structure 146 and the outer wall structure 148 extend substantially parallel with one another. The inner wall structure 146 includes a pair of walls 150a, 150b that receive the inner wall 138 of the upper member 132 therebetween. A fluid 152, such as, for example, water, oil, lubricant or other fluid, is substantially surrounded by the walls 150a, 150b, 154a, 154b. The amount of fluid 152 between the walls 150a, 150b and 154a, 154b measures a pressure change between the inhalation chamber 156 and the exhalation chamber 158, respectively. The amount of fluid 152 is not essential to the operation of the apparatus 130. The fluid 152 may be any fluid, although water is preferred because a patient or caretaker can refill the apparatus 130 with water, as needed.

Alternatively, this construction could be reversed by providing the inner wall 138 and the outer wall 140 on the lower member 134 and providing the inner wall structure 146 and the outer wall structure 148 on the upper member 132.

The fluid 152 allows the inner wall 138 to move relative to the walls 150a, 150b. The outer wall structure includes a pair of walls 154a, 154b that receive the outer wall 140 of the upper member 132 therebetween. The walls 154a, 154b substantially surround the outer wall 140 and the fluid 152, thereby allowing relative movement between the outer wall 140 and the walls 154a, 154b. The wall 150a defines an inspiration or inhalation chamber 156 and the walls 150b, 154a cooperate to define an exhalation chamber 158.

The fluid 152 is disposed between the upwardly extending walls 150a, 150b, 154a, 154b and substantially surrounds the inner and outer walls 138, 140. As shown in FIG. 19, the fluid between the wall 150a and the inner wall 138 is in communication with the inhalation chamber 156 and the fluid between the wall 150b and the inner wall 138 is in communication with the exhalation chamber 158. The fluid between the wall 154b and the outer wall 140 is in communication with an atmosphere and the fluid between the wall 154a and the outer wall 140 is in communication with the exhalation chamber 158.

Figure 20:
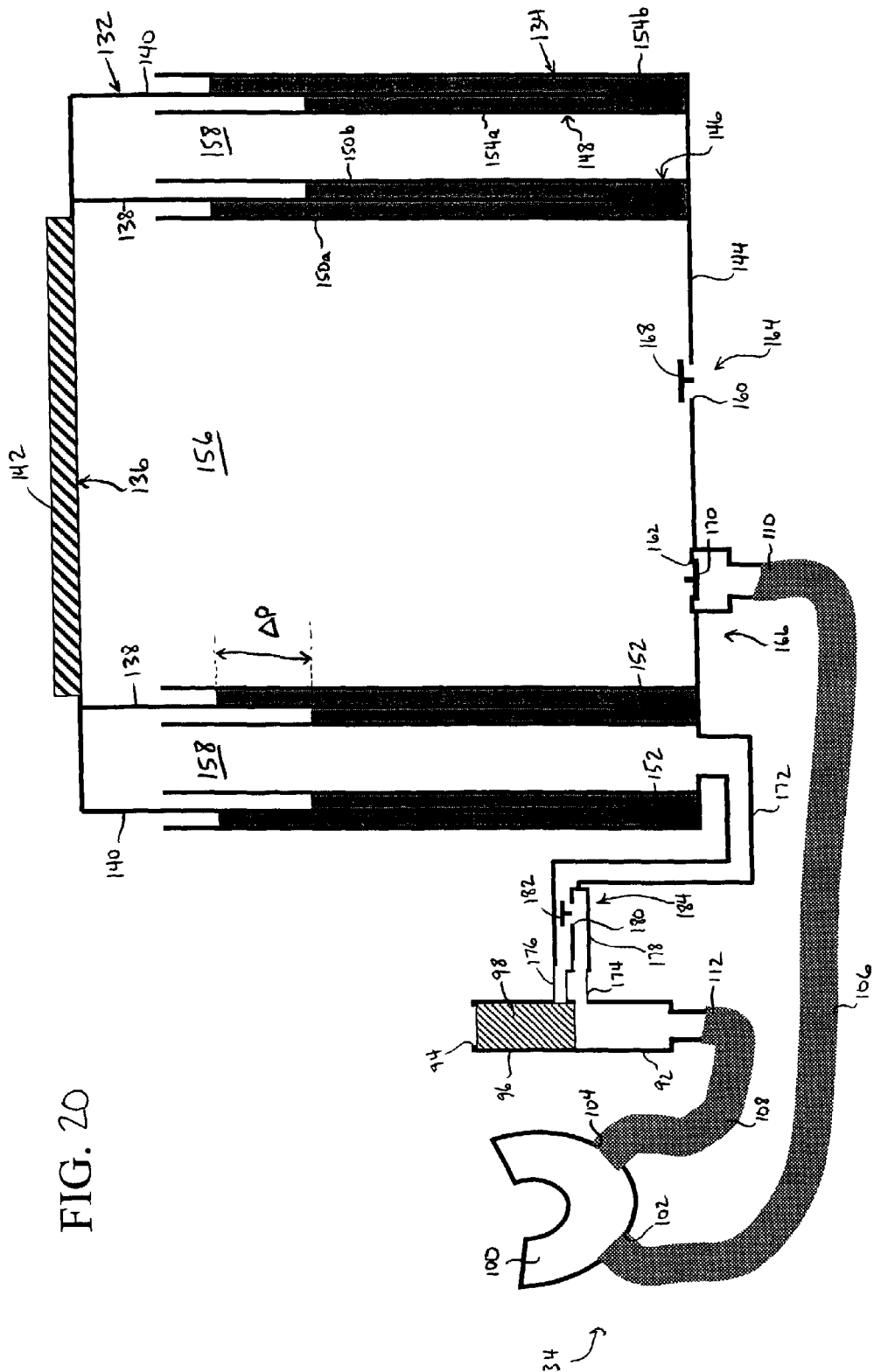
FIG. 20 is a schematic view of the breathable gas supply apparatus shown in FIG. 19 during a subsequent exhalation position thereof, wherein the patient is exhaling and the patient's exhaled gas moves the upper member to supply fresh breathable gas into the inhalation chamber.
Figure 22:
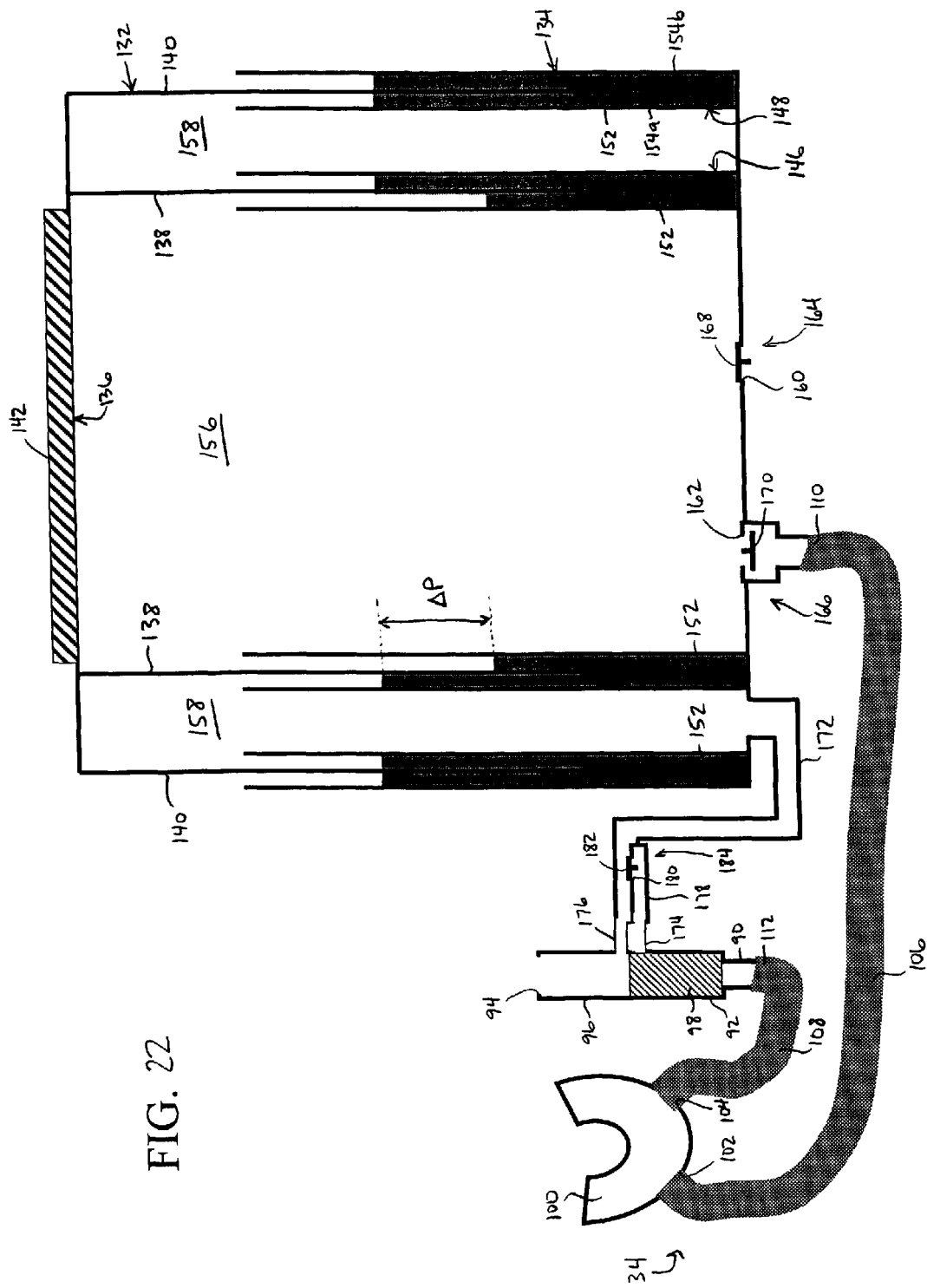
FIG. 22 is a schematic view of the breathable gas supply apparatus shown in FIG. 19 during subsequent initial inhalation positions thereof, wherein the patient is inhaling breathable gas collected in the inhalation chamber.
Figure 23:
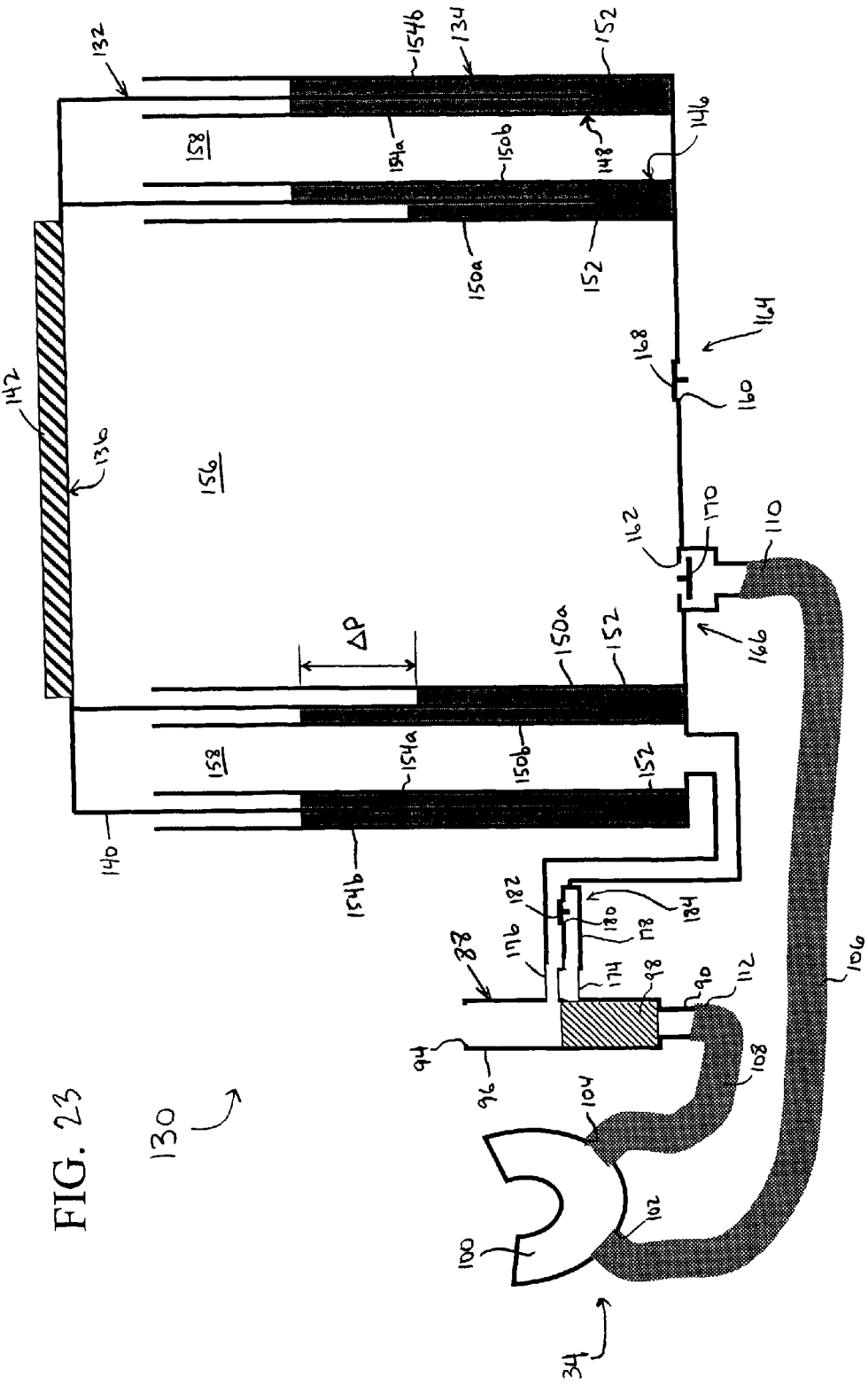
FIG. 23 is a schematic view of the breathable gas supply apparatus shown in FIG. 19 during a subsequent inhalation position thereof, wherein the patient is inhaling breathable gas collected in the inhalation chamber.

The fluid 152 can show a relative pressure difference between the inhalation chamber 156 and the exhalation chamber 158. The pressure difference, in the embodiment shown in FIGS. 19-23, can be shown by the height difference in the fluid level on opposite sides of the inner and outer walls 138, 140. For example, if the fluid level between the wall 154b and the outer wall 140 is substantially equal to the fluid level between the wall 154a and the outer wall 140, then the pressure difference between the atmosphere and the exhalation chamber 158 is minimal (FIG. 19). However, if the fluid level between the wall 150a and the inner wall 138 differs from the fluid level between the wall 150b and the inner wall 138, the inhalation chamber 156 and the exhalation chamber 158 have differing pressures (FIGS. 20 and 22-23). As shown in FIGS. 20 and 22-23, the pressure difference between the inhalation chamber 156 and the exhalation chamber 158 is represented by the height difference ΔP between the respective fluid levels.

Although the fluid 152 is illustrated in FIG. 19 as being substantially the same level both between the walls 154a, 154b and the outer wall 140 and between the walls 150a, 150b and the inner wall 138, the fluid 152 could be provided to be different levels between those walls. The amount of fluid 152 between the walls 154a, 154b and the outer wall 140 and between the walls 150a, 150b and the inner wall 138 measures a pressure change between the inhalation chamber 156 and the exhalation chamber 158. Thus, the amount of fluid between the walls 138, 140, 150a, 150b, 154a and 154b is not essential to the operation of the apparatus 130.

As the upper member 132 moves relative to the lower member 134, in a downward direction, the fluid 152 will be displaced by the inner and outer walls 138, 140. The pressure in either the inhalation chamber 156 or the exhalation chamber 158 does not necessarily change, i.e., increase or decrease, even though fluid 152 is being displaced between the walls 150a, 38, 150b and 154a, 40, 154b.

The upper member 132 is constructed and arranged to raise in response to a force of patient expiration to draw fresh air into the inhalation chamber 156 and to allow air exhaled by the patient to accumulate within the exhalation chamber 158 during an exhalation phase of a respiratory cycle of the patient. The upper member 132 is also constructed and arranged to provide a source of pressurized fresh air to the patient and to provide a force to expunge the exhaled air accumulated within the exhalation chamber 158 during an inhalation phase of the respiratory cycle of the patient.

The lower wall 144 includes a pair of valve seats 160, 162 machined therein. The valve seats 160, 162 are substantially identical in construction and operation to the valve seats 46, 48. The lower wall 144 cooperates with a first and second gas supply valve 164, 166 and sealing structures 168, 170 to permit fluid communication through the valve seats 160, 162, respectively. The first and second gas supply valves 164, 166 and the sealing structures 168, 170 and are substantially identical in construction and operation to the first and second gas supply valves 50, 52 and the sealing structures 54, 56. The gas supply valves 164, 166 may be disposed within valve housings, such as the housing 58, for example.

Extending from the exhalation chamber 158 is an air passageway 172. The air passageway 172 permits air passage to and from the exhalation chamber 158 during the operation of the breathable gas supply apparatus 130, as will be described in further detail below. The air passageway 172 connects to an exhalation inlet 174 and a gas washout vent 176, which are connected with the exhalation chamber 158 in fluid communication.

An exhalation valve housing 178 is positioned in fluid communication with the exhalation inlet 174 and forms a valve seat 180, which is configured to receive a sealing structure 182. The valve seat 180 and the sealing structure 182 constitute an exhalation valve 184, which is substantially identical in construction and operation to the exhalation valve 76. The exhalation inlet 174 and the gas washout vent 176 are connected to the valve 88 and the air directing member 98, both of which are described above and illustrated in FIG. 1. The respiratory mask assembly 34 can be connected to the exhalation chamber 158 of the apparatus 130 in fluid communication with the valve 88 and the air directing member 98.

Alternatively, seals, such as piston rings, for example, can be used in the breathable gas supply apparatus 130 to provide an effective seal between the inhalation chamber 156 and the exhalation chamber 158. For example, the seals may be positioned between the upper ends of the upwardly extending walls 150a, 150b and the inner wall 138 and may be positioned between the upper ends of the upwardly extending walls 154a, 154b and the outer wall 140. In addition to providing an effective seal between the inhalation chamber 156 and the exhalation chamber 158, the seals can also act as a stop for the upper member 132 when moved into a storing position, wherein the upper wall 136 of the upper member 132 contacts the upwardly extending walls 150a, 150b, 154a, 154b and the inner and outer walls 138, 140 contact the lower wall 144 of the lower member 134. In the storing position, for example, the apparatus 130 can be stored while not in use by the patient.

Now, reference is made to FIGS. 19-23, which illustrate operation of the breathable gas supply apparatus 130 when positioned in communication with a spontaneously breathing patient. The respiratory mask 100 is shown and can be firmly secured over the patient's nose, mouth, or face, as described above. Motions of the movable parts of the apparatus 130 are illustrated in subsequent positions during operation thereof. During operation of the apparatus 130, the fluid 152 can indicate the pressure differences between the inhalation and exhalation chambers 156, 158. The pressure difference is indicated as ΔP in FIGS. 20 and 22, and can be read in a manner that is similar to the way a pressure manometer is read.

FIG. 19 shows the apparatus 130 in an initial position, just before patient exhalation. The valves 164, 166 and 184 are closed so as to prevent air passage therethrough and the upper member 132 is positioned in a gas supplying position, wherein fresh air has been drawn into the inhalation chamber 156 and exhaled air has been accumulated in the exhalation chamber 158. Similar to the apparatus 30, the air directing member 98 is disposed at the lower portion 92 of the valve 88 in its first position. When the apparatus 130 is in this initial position, and a patient inhales, for example, the valves 164, 166 can be opened to allow the patient to inhale breathable air from the atmosphere. In this case, the inhalation of the patient would open the valve 166. A change in pressure in the inhalation chamber 40 would be produced, which would cause valve 164 to open to allow breathable air into the inhalation chamber 156 and to the patient through valve 166 from the atmosphere.

As the patient exhales, as shown in FIG. 20, exhaled gas, such as carbon dioxide, is prevented from flowing through the port 102 and the conduit 106 by the air supply valve 166. The exhaled gas flows out of the port 104 and through the conduit 108. The pressure within the mask 100 increases until the pressure reaches a certain level capable of moving the air directing member 98. The pressure level for moving the air directing member 98 may be, for example, 11 cms water pressure. When the pressure reaches the certain pressure level, for example, as shown in FIG. 20, the air directing member 98 moves to its second position. In its second position, the air directing member 98 directs the exhaled gas to flow through the exhalation inlet 174 and the exhalation valve 184 so that exhaled gas begins to fill the exhalation chamber 158.

As exhalation continues, the pressure within the exhalation chamber 158 continues to increase until the pressure exceeds the weight of the upper member 132 and the weight 142. When the pressure reaches an amount substantially equal to the weight of the upper member 132 and the weight 142, for example, the upper member 132 begins to move upward with respect to the lower member 134. As the upper member 132 moves upwardly, exhaled air from the patient accumulates in the exhalation chamber 158. The pressure within the apparatus 130 draws the gas supply valve 164 into its open position such that a supply of fresh, breathable gas is drawn therethrough into the inhalation chamber 156 from atmosphere.

Figure 21:
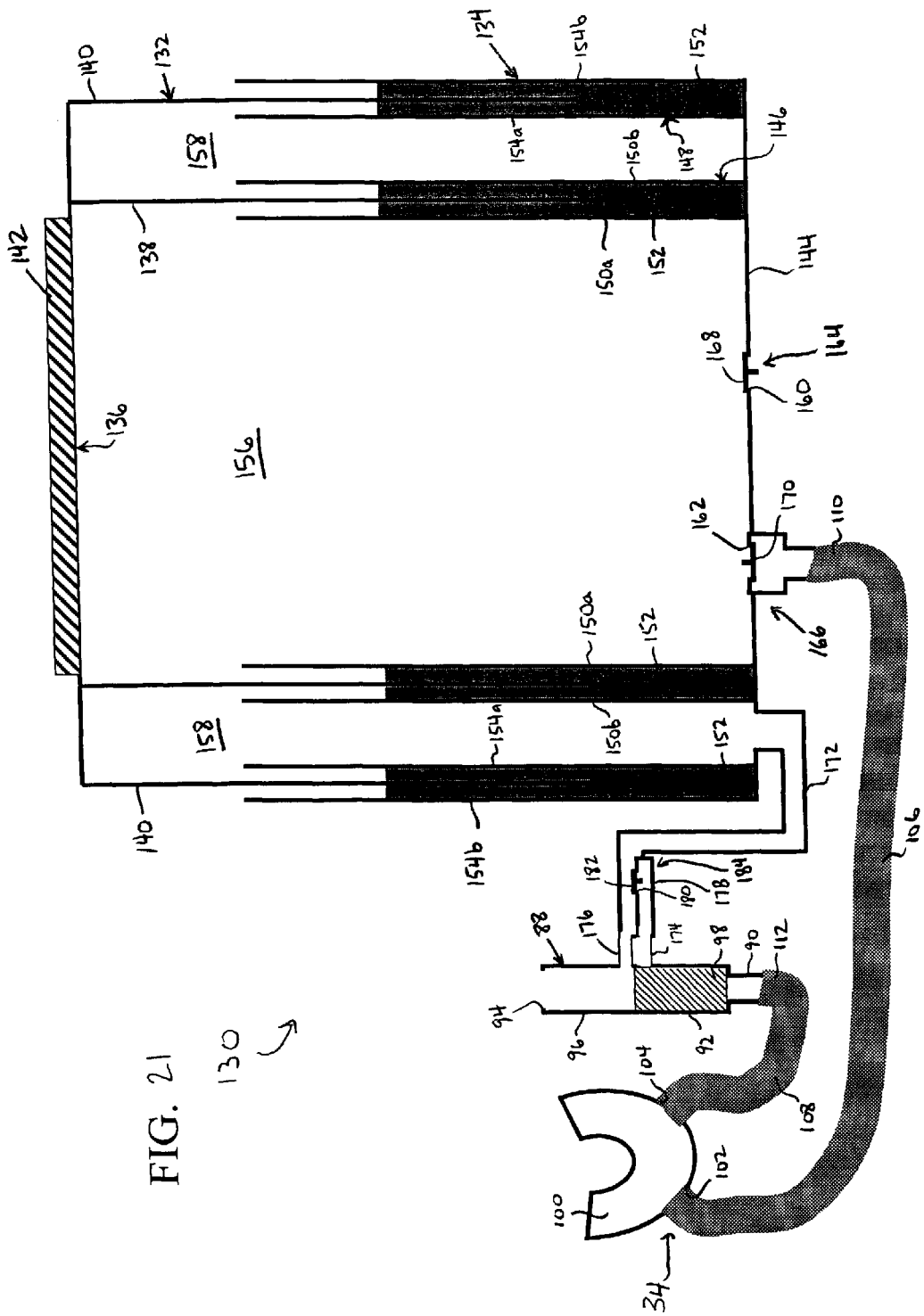
FIG. 21 is a schematic view of the breathable gas supply apparatus shown in FIG. 19 at the moment the patient stops exhaling, but before inhalation begins.

During exhalation of the patient, the upper member 132 moves against the force of gravity and the weight 142 from a lowered position (where the upper wall 136 is moved into close proximity to the upwardly extending walls 150a, 150b, 154a, 154b and where the inner and outer walls 138, 140 is moved into close proximity to the lower wall 144) to an intermediate position (FIG. 21). FIG. 21 shows the apparatus 130 in its intermediate position, wherein the patient stops exhaling, but prior to inhalation. The extent of upward movement of the upper member 132 will vary depending on the patient's exhaled breath.

During exhalation, mechanical work done by the patient is stored in the form of potential energy, as the upper member 132 moves upwardly. When exhalation ceases, the upper member 132 is disposed in its intermediate position, as shown in FIG. 21 and the air directing member 98 moves into its first position to allow exhaled air to escape to atmosphere. Fresh breathable gas is continuously drawn into the inhalation chamber 156 until the upper member 132 reaches its uppermost position.

After exhalation ceases and prior to inhalation, the valves 164, 166, 184 close to prevent gas from passing therethrough (as shown in FIG. 21). FIG. 21 could be representative of a situation where a patient is exhaling, but the force at which the patient is exhaling is not great enough to lift the air directing member 98.

FIGS. 22 and 23 are sequential views of the breathable gas supply apparatus 130 illustrating the patient inhaling a supply of fresh, breathable gas, such as oxygen, from the inhalation chamber 156. As a patient begins to inhale, the air supply valve 166 opens to allow air passage therethrough and the patient may draw fresh, breathable air from the inhalation chamber 156 into the mask 100 through the air supply valve 166, the flexible conduit 106 and the inhalation port 102. The supply of fresh, breathable gas enters the patient's lungs until the inhalation phase of respiratory cycle of the patient stops.

When inhalation begins, the valves 164 and 184 close to prevent gas from flowing therethrough and so that the inhalation chamber 156 can maintain a supply of fresh, breathable gas therein. During inhalation, the patient utilizes only stored mechanical energy, which is then transferred to the patient by the upper member 132 to assist the patient's respiratory effort as the upper member 132 moves downwardly.

During subsequent inhalation of the patient, the force of gravity in combination with the weight 142 help move the upper member 132 relative to the lower member 134 in a downward direction. Downward movement of the upper member 132 forces fresh air out of the inhalation chamber 156 and allows exhaled air from the patient accumulated in the exhalation chamber 158 to escape to atmosphere.

If the patient continues to inhale after inhaling the entire supply of breathable gas in the inhalation chamber 156 (i.e., the patient needs more air than accumulated in the inhalation chamber 156), the valves 164, 166 can be opened to allow the patient to inhale additional breathable air from the atmosphere. In this case, the inhalation of the patient would open the valve 166. A change in pressure in the inhalation chamber 156 would be produced, which would cause valve 164 to open to allow breathable air into the inhalation chamber 156 and to the patient through valve 166 from the atmosphere.

When the patient stops inhaling, and just before patient exhalation, the apparatus 130 will be positioned in its initial position, as shown in FIG. 19. From its initial position, the apparatus 130 operates as shown and described above with respect to FIGS. 20-23.

As the patient continues respiration, i.e., breathing, by taking subsequent breaths, the apparatus 130 will continuously operate as described above, specifically in accordance with FIGS. 20-23, which constitute one full breath (exhalation and inhalation) of the patient. FIGS. 22-23 constitute the inhalation phase of the patient's breath (respiratory cycle) and FIG. 20 constitutes the exhalation phase of the patient's breath (respiratory cycle). However, when the mask 100 is removed from the patient or if the patient stops exhaling, the apparatus 130 will return to its lowered position shown in FIG. 19, which may be utilized when storing the apparatus 130, for example.

FIGS. 24-28 show a breathable gas supply apparatus 230 for a patient, which is another embodiment of the breathable gas supply apparatus 130. In the following description of the embodiment illustrated in FIGS. 24-28, only the points of difference of the embodiment from the embodiment illustrated in FIGS. 19-23 will be described. That is, in those embodiments, the constituent parts the same as those in the first embodiment are referenced correspondingly in the drawings and the description about them will be omitted. The breathable gas supply apparatus 230 operates in substantially the same manner as the breathable gas supply apparatus 130, but realizes an alternative construction.

Figure 26:
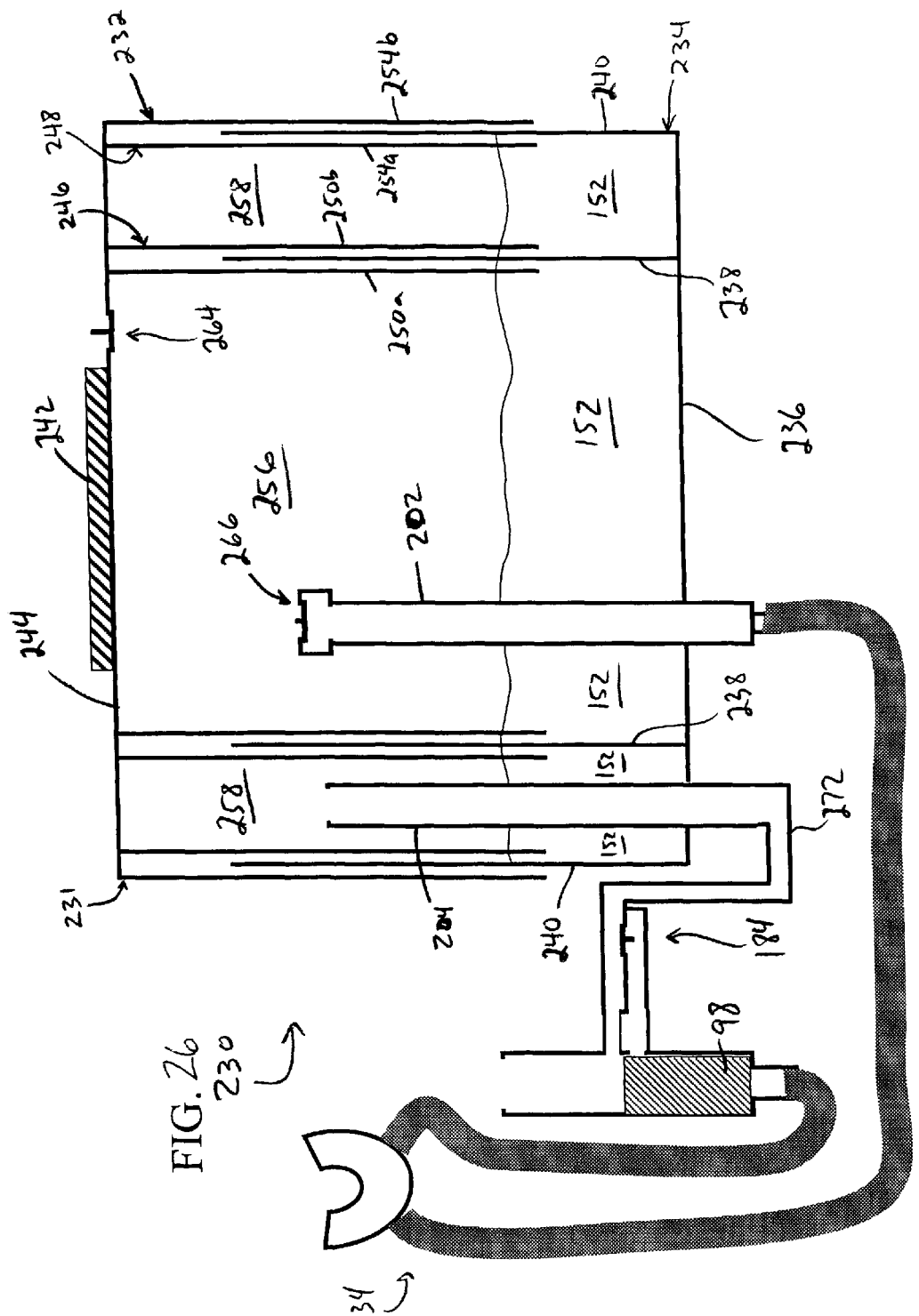
FIG. 26 is a schematic view of the breathable gas supply apparatus shown in FIG. 24 at the moment the patient stops exhaling, but before inhalation begins.
Figure 27:
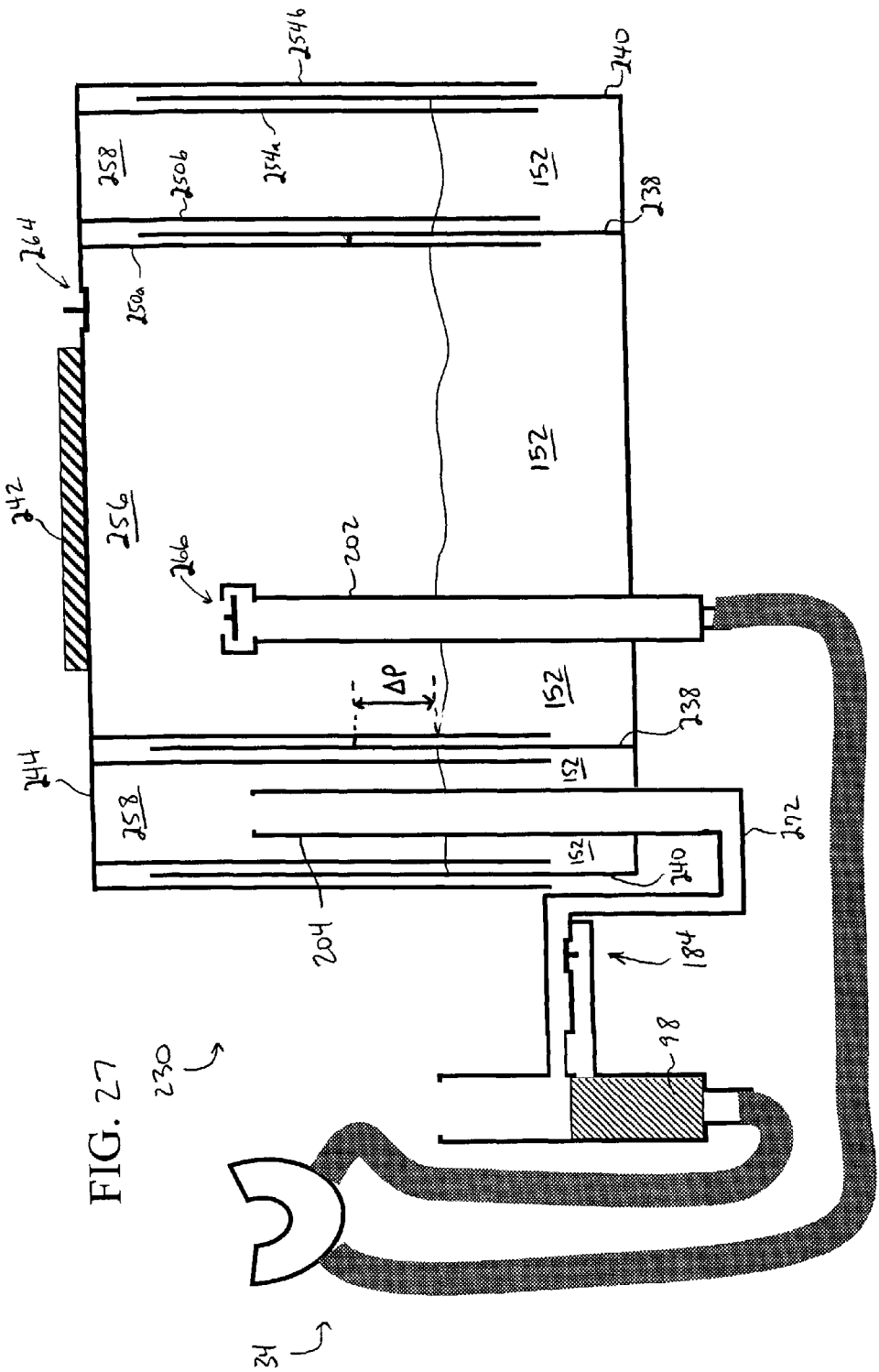
FIG. 27 is a schematic view of the breathable gas supply apparatus shown in FIG. 24 during an inhalation position thereof, wherein the patient is inhaling breathable gas collected in the inhalation chamber.
Figure 28:
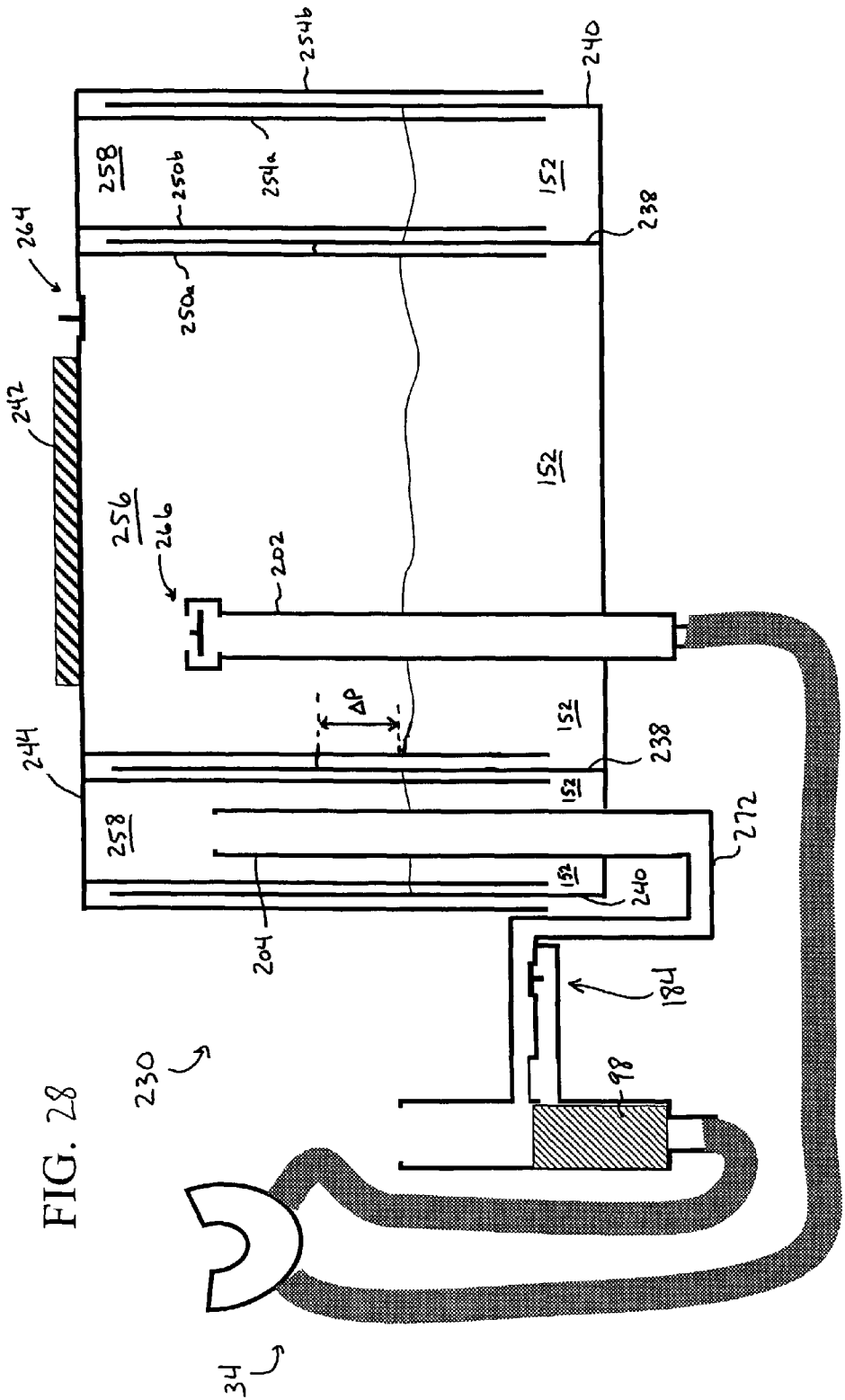
FIG. 28 is a schematic view of the breathable gas supply apparatus shown in FIG. 24 during a subsequent inhalation position thereof, wherein the patient is inhaling breathable gas collected in the inhalation chamber.
Figure 29:
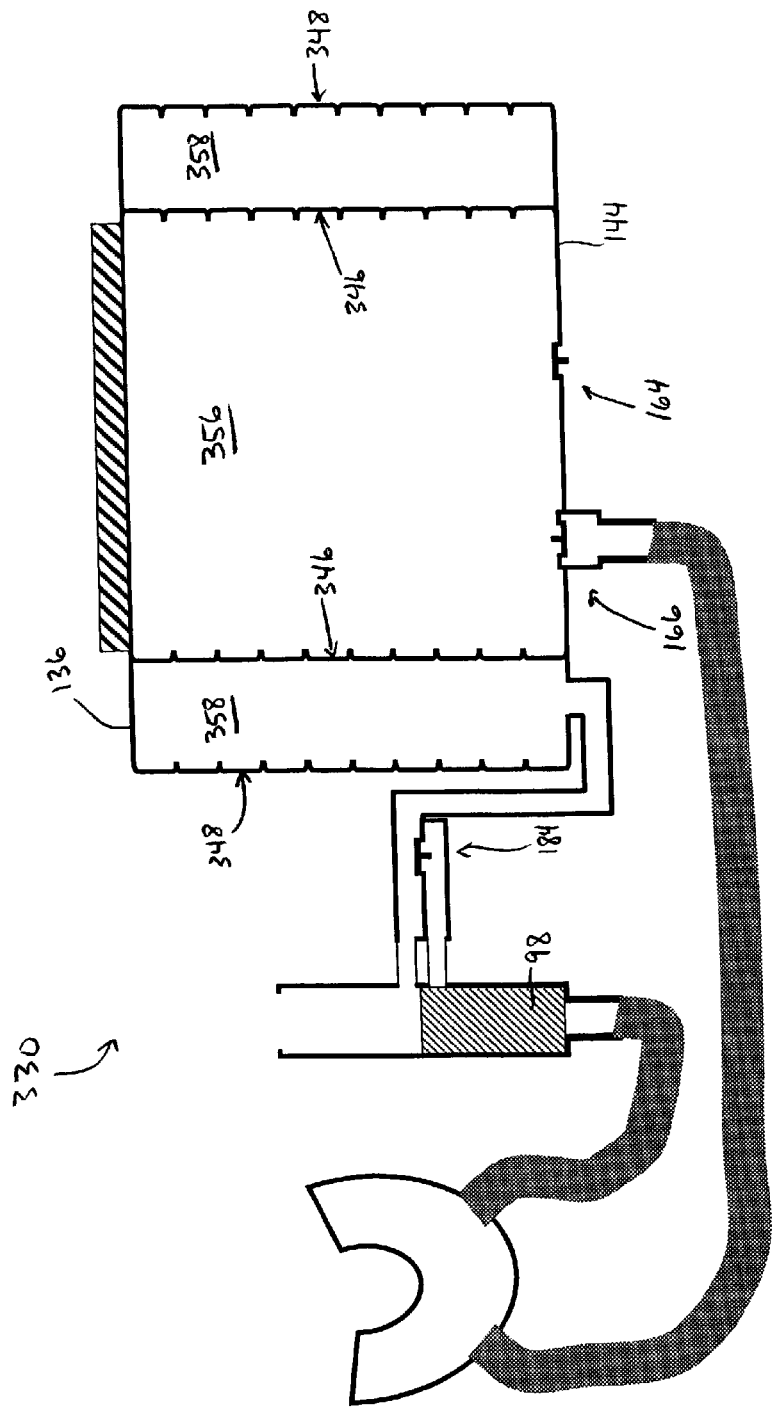
FIG. 29 is a schematic view of a breathable gas supply apparatus in an initial position thereof according to still another embodiment of the present invention.
Figure 30:
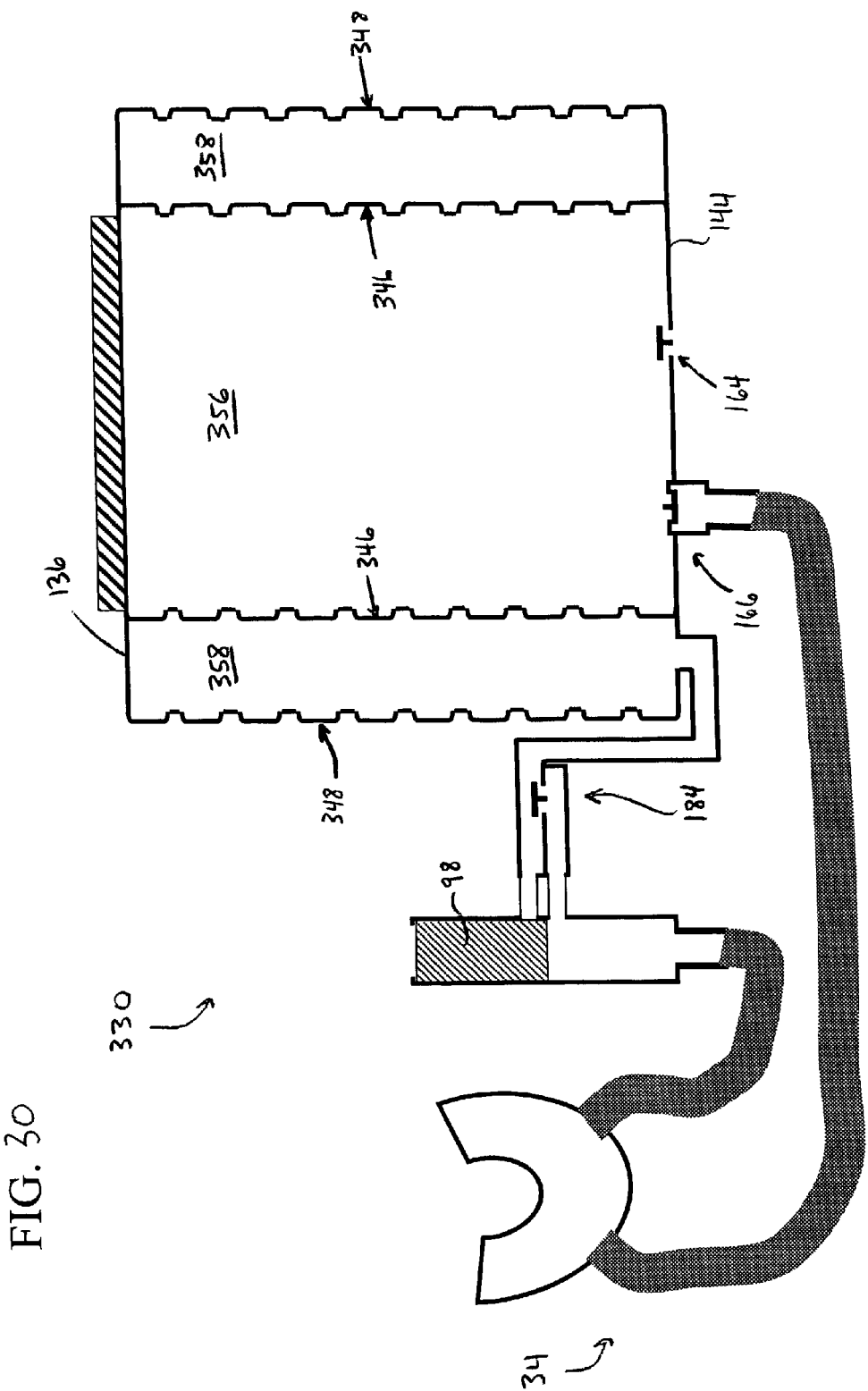
FIG. 30 is a schematic view of the breathable gas supply apparatus shown in FIG. 29 during a subsequent exhalation position thereof, wherein the patient is exhaling and the patient's exhaled gas moves the upper member to supply fresh breathable gas into the inhalation chamber.
Figure 31:
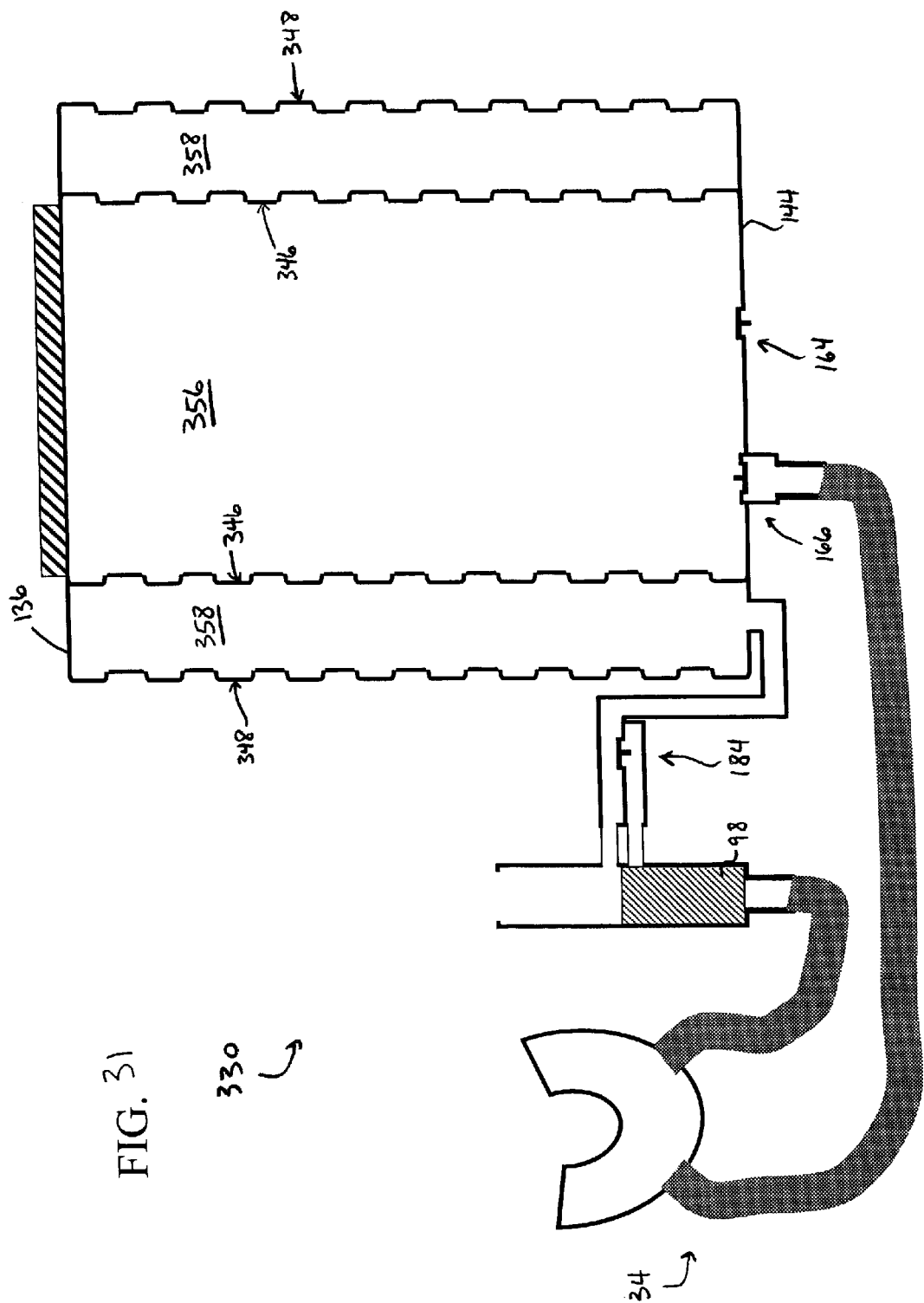
FIG. 31 is a schematic view of the breathable gas supply apparatus shown in FIG. 29 at the moment the patient stops exhaling, but before inhalation begins.
Figure 32:
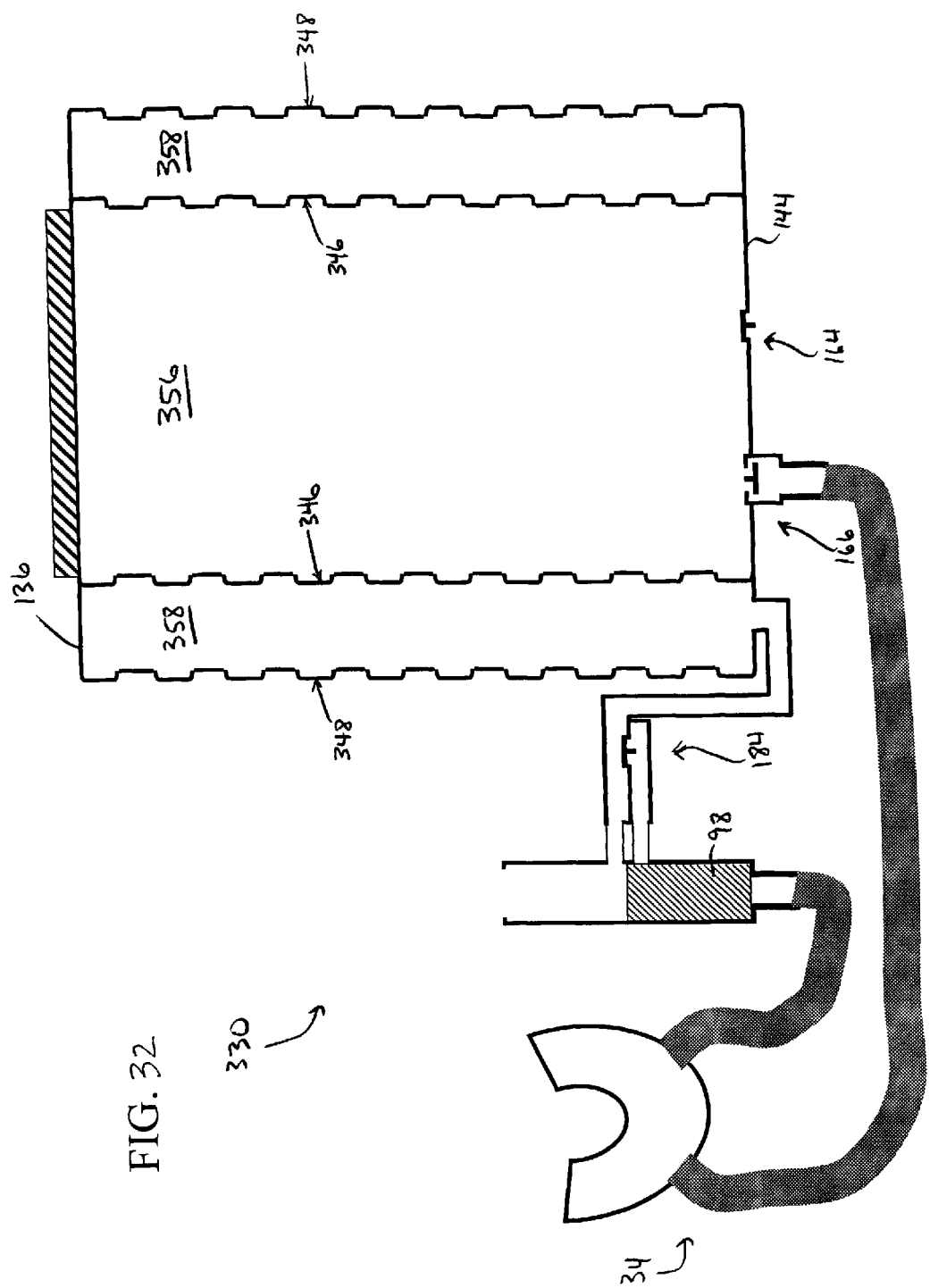
FIG. 32 is a schematic view of the breathable gas supply apparatus shown in FIG. 29 during a subsequent inhalation position thereof, wherein the patient is inhaling breathable gas collected in the inhalation chamber.
Figure 33:
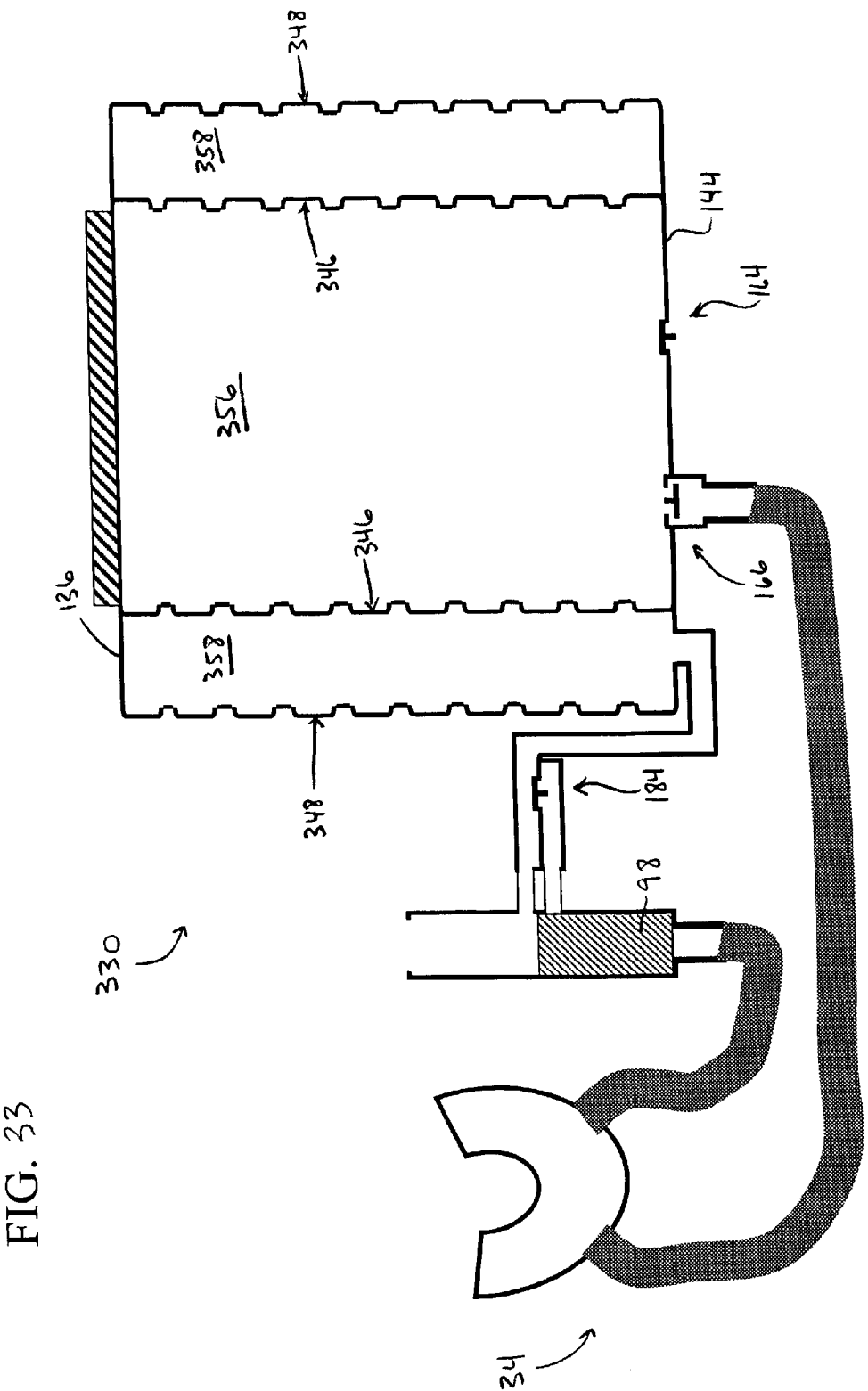
FIG. 33 is a schematic view of the breathable gas supply apparatus shown in FIG. 29 during a subsequent inhalation position thereof, wherein the patient is inhaling breathable gas collected in the inhalation chamber.

The breathable gas supply apparatus 230 includes a housing 231 having an upper member 232 and a lower member 234 in fluid communication with one another so that the upper member 232 can move with respect to the lower member 234 (FIG. 26). The upper member 232 and the lower member 234 can be in the form of concentric cylinders or may be configured to have any other complementing configuration, such as having rectangular or round cross-sectional portions. Although the upper member 232 and the lower member 234 can be formed to be any dimensions or size, the upper member 232 and the lower member 234 might have a height of 10-15 centimeters, an inner diameter of 10-15 centimeters and a volume of 0.75-1.5 liters, if in the form of concentric cylinders, for example.

Figure 24:
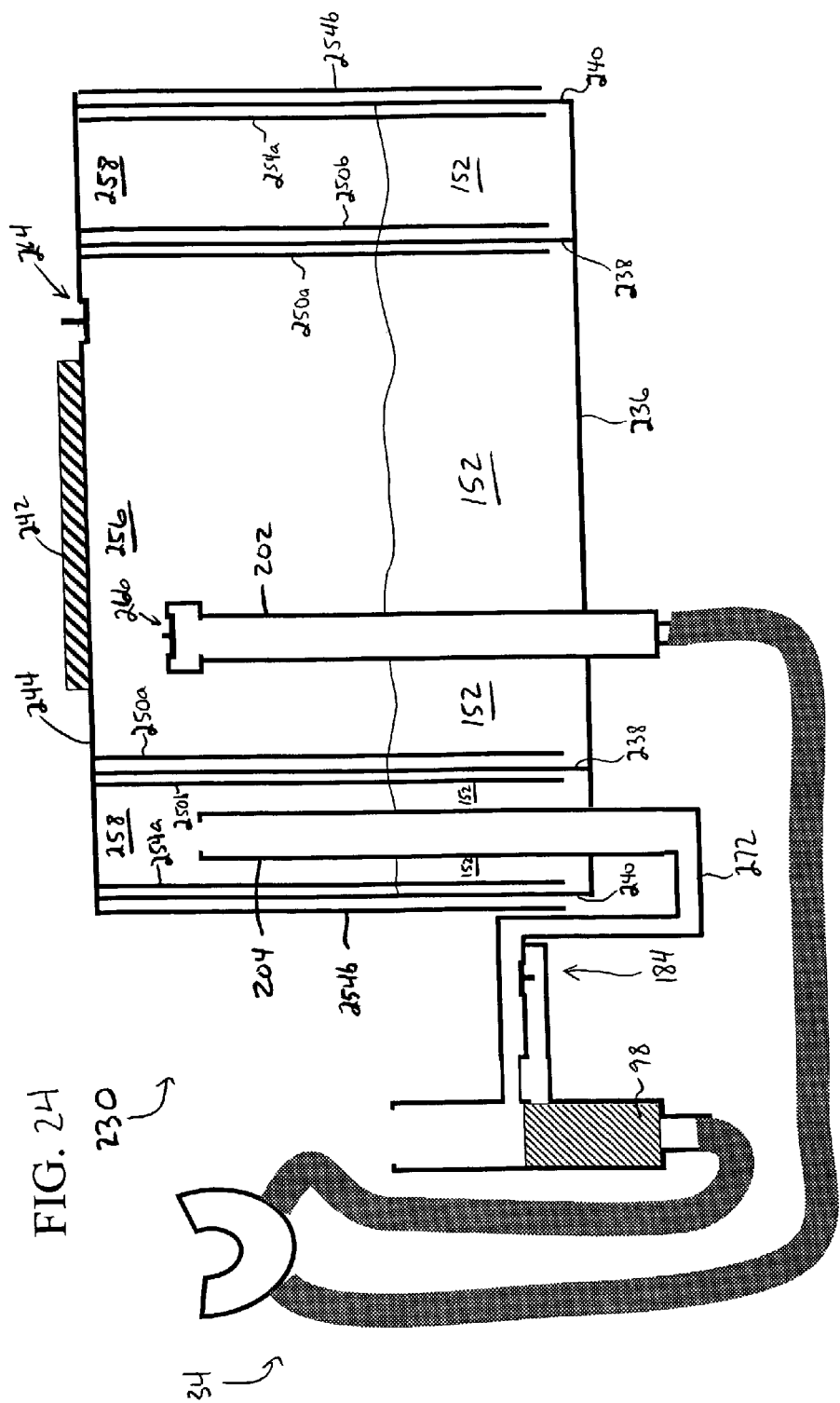
FIG. 24 is a schematic view of a breathable gas supply apparatus in an initial position thereof according to yet another embodiment of the present invention.
Figure 25:
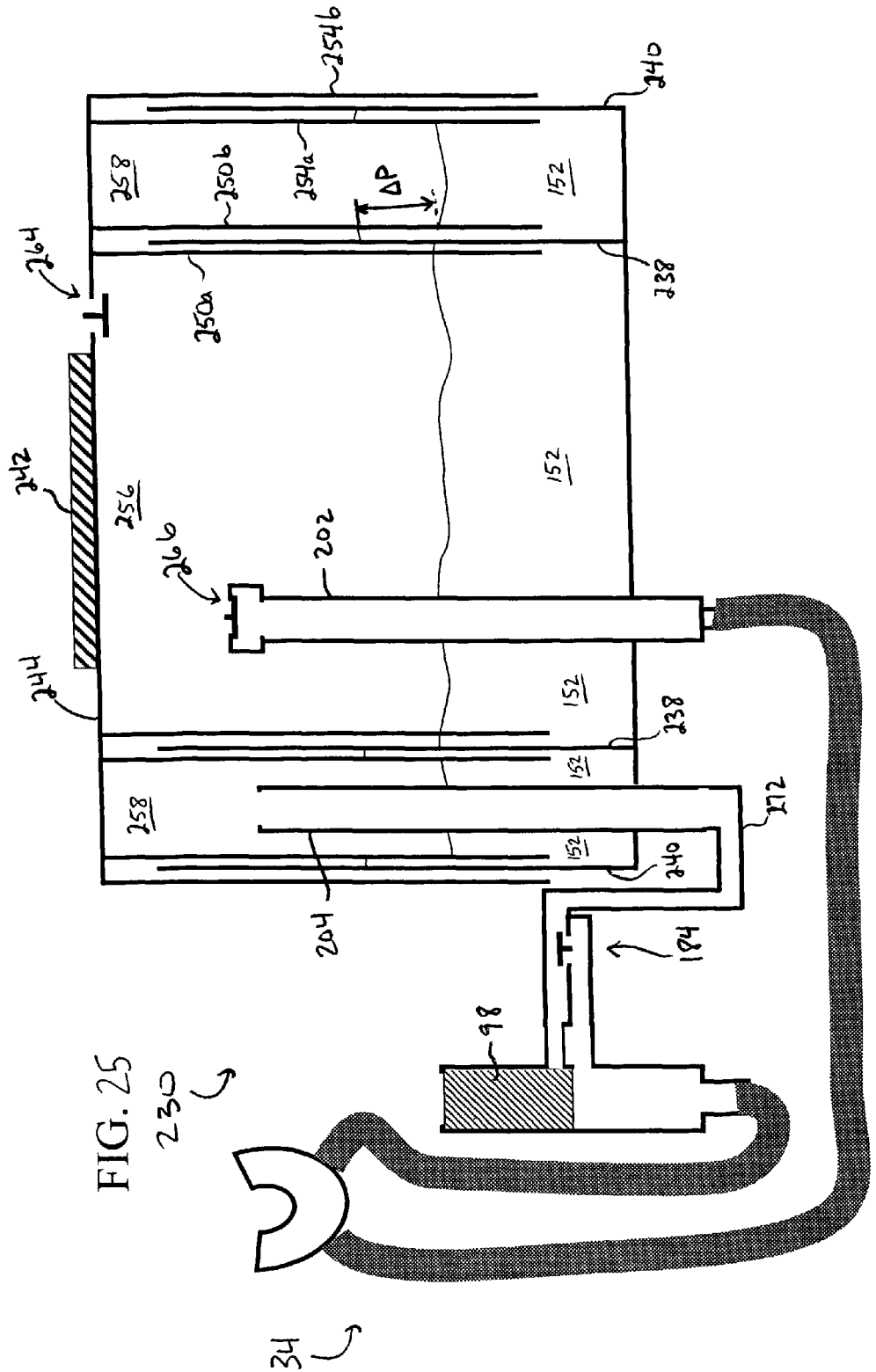
FIG. 25 is a schematic view of the breathable gas supply apparatus shown in FIG. 24 during a subsequent exhalation position thereof, wherein the patient is exhaling and the patient's exhaled gas moves the upper member to supply fresh breathable gas into the inhalation chamber.

The lower member 234 includes a lower wall 236 having an inner wall 238 and an outer wall 240 upwardly extending therefrom (FIG. 24). The inner wall 238 and the outer wall 240 extend substantially parallel with one another.

As shown in FIG. 26, the upper member 232 is in the form of an upper wall 244 having an inner wall structure 246 and an outer wall structure 248 upwardly extending therefrom. The inner wall structure 246 and the outer wall structure 248 extend substantially parallel with one another. The inner wall structure 246 includes a pair of walls 250a, 250b that receive the inner wall 238 of the lower member 234 therebetween. A fluid 152, such as, for example, water, oil, lubricant or other fluid, is substantially surrounded by the inner and outer walls 238, 240. For example, an amount of fluid 152 is surrounded by the inner wall 238 to have a certain fluid level in the inhalation chamber 256 and another amount of fluid is surrounded by the outer wall 240 to have a certain fluid level in the exhalation chamber 258. Although the fluid 152 is illustrated as being substantially the same level in both the inhalation chamber 256 and the exhalation chamber 258, the fluid 152 could be provided to be different levels in the inhalation chamber 256 and the exhalation chamber 258, for example. The amount of fluid 152 in the inhalation chamber 256 and the exhalation chamber 258 measures a pressure change between the inhalation chamber 256 and the exhalation chamber 258, and is not essential to the operation of the apparatus 230. The fluid 152 may be any fluid, although water is preferred because a patient or caretaker can refill the apparatus 230 with water, as needed.

Alternatively, this construction could be reversed by providing the inner wall 238 and the outer wall 240 on the upper member 232 and providing the inner wall structure 246 and the outer wall structure 248 on the lower member 234.

A weight 242 can form a portion of the upper wall 236 244 (shown positioned between the inner wall structure 246 of the upper member 232 in FIG. 24), for example, or can be fixedly attached to the upper wall 236 244 by a fastener, bonding material or adhesive.

The inner wall 238 may move relative to the walls 250a, 250b. The outer wall structure 248 includes a pair of walls 254a, 254b that receive the outer wall 240 of the lower member 234 therebetween. The walls 254a, 254b substantially surround the outer wall 240 and the wall 254a cooperates with the outer wall 240 to substantially surround the fluid 152, thereby allowing relative movement between the outer wall 240 and the walls 254a, 254b. The wall 250a defines the inspiration or inhalation chamber 256 and the walls 250b, 254a cooperate to define an exhalation chamber 258. The inhalation chamber 256 and the exhalation chamber 258 are substantially the same in construction and operation as the inhalation chamber 156 and the exhalation chamber 158.

A first gas supply valve 264 is substantially identical in construction and operation to the first gas supply valve 50 shown in FIG. 1 and the first gas supply valve 164 shown in FIG. 19. The gas supply valve 266 is the same as the gas supply valve shown in FIG. 19, but is disposed within a longitudinally extended valve housing 202. The valve housing 202 extends through the lower wall 236 and the fluid 152 to communicate with the inhalation chamber 256.

An extended air passageway 204 extends through the lower wall 236 and the fluid 152 to communicate with the exhalation chamber 258. The air passageway 204 extends from the exhalation chamber 258 to an air passageway 272. The air passageways 204, 272 permit air passage to and from the exhalation chamber 258 during the operation of the breathable gas supply apparatus 230 in a similar manner as described above with respect to the air passageway 172 of the breathable gas supply apparatus 130.

In the breathable gas supply apparatus 230 as shown in FIGS. 25-28, the valves 264, 266 and 184 and the air directing member 98 operate in the same manner (for the same phases of the respiratory cycle of the patient) as described above with respect to the breathable gas supply apparatus 130 as shown in FIGS. 20-23. Particularly, the valves 264 and 266 operate in substantially the same manner as described above with respect to the valves 164 and 166 of the with respect to the breathable gas supply apparatus 130.

FIGS. 29-33 show a breathable gas supply apparatus 330 for a patient, which is another embodiment of the breathable gas supply apparatus 130. In the following description of the embodiment illustrated in FIGS. 29-33, only the points of difference of the embodiment from the embodiment illustrated in FIGS. 19-23 will be described. That is, in those embodiments, the constituent parts the same as those in the first embodiment are referenced correspondingly in the drawings and the description about them will be omitted.

The breathable gas supply apparatus 330 operates in substantially the same manner as the breathable gas supply apparatus 130, but realizes a more simplified construction in some respects. For example, and similarly to the apparatus 130, the breathable gas supply apparatus 330 includes inner wall structure 346 and outer wall structure 348 that extend between an upper wall 136 and a lower wall 144. However, in the apparatus 330, the inner wall structure 346 and the outer wall structure 348 are formed by flexible mechanical structures, such as bellows or concertinas. The inner and outer flexible mechanical structures 346, 348 may be coupled to the upper wall 136 and the lower wall 144 by fasteners, bonding material or adhesive, for example. The inner flexible mechanical structure 346 defines an inhalation chamber 356 and the inner and the outer flexible mechanical structures 346, 348 cooperate to define an exhalation chamber 358. As shown in FIGS. 29-33, the inhalation chamber 356 is substantially the same in operation as the inhalation chamber 156 (FIGS. 19-23) and the exhalation chamber 358 is substantially the same in operation as the exhalation chamber 158 (FIGS. 19-23).

FIGS. 29-33 show that the inner and outer flexible mechanical structures 346, 348 contract during a patient inhalation phase of the respiratory cycle of the patient and expand during a patient exhalation phase of the respiratory cycle of the patient. The valves 164, 166 and 184 and the air directing member 98 operate in the same manner (for the same phases of the respiratory cycle of the patient) as described above with respect to the breathable gas supply apparatus 130.

While the principles of the invention have been made clear in the illustrative embodiments set forth above, it will be apparent to those skilled in the art that various modifications may be made to the structure, arrangement, proportion, elements, materials, and components used in the practice of the invention.

For example, an external power source could be used to supply power to at least one of the piston 78, the air directing member 98, and the upper members 132, 232 to pressurize the inhalation chamber 40, 156, 256. Both the piston 78 and the air directing member 98 could be powered or one of the upper members 132, 232 and the air directing member 98 could be powered. That way, electrical power could be used to assist respiratory effort. For example, in the apparatus 30, the inhalation chamber 40 can be pressurized to move the weight 86 and the piston 78 into the gas receiving position thereof, during an initial patient inhalation phase of the respiratory cycle of the patient. In the apparatus 130, the inhalation chamber 156 could also be pressurized and in the apparatus 230, the inhalation chamber 256 could also be pressurized, for example. The power source could be low-powered and might use battery power or AC current, for example.

An external power source could also be used to supply power to the upper wall 136 of the breathable gas supply apparatus 330 to contract or to expand the inner and outer flexible mechanical structures 346, 348 to pressurize the inhalation chamber 356, for example.

The external power source could be implemented in the breathable gas supply apparatus in other ways as well. For example, the breathable gas supply apparatus may comprise a powered breathable gas supply system and a power supply. The power supply can be connected to the powered breathable gas supply system to assist the patient's respiratory effort, as described above, for example.

The foregoing preferred specific embodiments have been shown and described for the purpose of illustrating the functional and structural principles of this invention and are subject to change without departure from such principles.

What is claimed is:

1. A breathable gas supply apparatus for a patient, comprising:
   a housing having an inspiration chamber and an exhalation chamber, both the inspiration chamber and exhalation chamber being structured to selectively communicate with the atmosphere;
   a flexible mechanical structure provided to the housing; and
   a respiratory mask assembly in communication with the inspiration chamber and the exhalation chamber,
   wherein the flexible mechanical structure is constructed and arranged to:
   (1) expand in response to a force of patient expiration to draw fresh air from the atmosphere into the inspiration chamber and to allow air exhaled by the patient to accumulate within the exhalation chamber during an exhalation phase of a respiratory cycle of the patient, the expanded flexible mechanical structure adapted to store mechanical energy in the form of mechanical work done by the patient during the exhalation phase, and
   (2) contract in response to patient inspiration to provide a source of pressurized fresh air at a substantially constant positive pressure from the inspiration chamber to the patient and to provide a force that utilizes stored mechanical energy in the form of mechanical work done by the patient to expunge the exhaled air accumulated within the exhalation chamber into the atmosphere during an inhalation phase of the respiratory cycle of the patient,
   wherein the flexible mechanical structure includes a weight that is at least partially determinative of the pressure.

2. A breathable gas supply apparatus as in claim 1, wherein the flexible mechanical structure includes an inner flexible mechanical structure and an outer flexible mechanical structure.

3. A breathable gas supply apparatus as in claim 2, wherein the housing includes an upper wall and a lower wall spaced from the upper wall, the inner flexible mechanical structure and the outer flexible mechanical structure being disposed between the upper wall and the lower wall of the housing.

4. A breathable gas supply apparatus as in claim 3, wherein each of the inner flexible mechanical structure and the outer flexible mechanical structure includes a concertina.

5. A breathable gas supply apparatus as in claim 4, wherein the inner flexible mechanical structure defines the inspiration chamber and the inner flexible mechanical structure and the outer flexible mechanical structure cooperate to define the exhalation chamber.

6. A breathable gas supply apparatus as in claim 1, wherein the substantially constant positive pressure is within a range of 2-20 $cmH_2O$.

7. A method of generating a source of pressurized breathable gas for a patient, the method comprising:
   drawing fresh air from the atmosphere into an inspiration chamber and allowing air exhaled by the patient to accumulate within an exhalation chamber in response to patient expiration during an exhalation phase of the respiratory cycle of the patient;
   storing mechanical energy in the form of mechanical work done by the patient during the exhalation phase;
   pressurizing and providing the fresh air from the inspiration chamber to the patient at a substantially constant positive pressure and expunging the exhaled air accumulated within the exhalation chamber into the atmosphere in response to patient inspiration during an inhalation phase of the respiratory cycle of the patient; and
   utilizing only the stored mechanical energy to assist patient respiratory effort during the inhalation phase,
   wherein storing mechanical energy includes moving a movable structure with a weight that is at least partially determinative of the pressure.

8. A method as in claim 7, wherein the utilizing comprises transferring the stored mechanical energy to assist respiratory effort during the inhalation phase of the respiratory cycle of the patient.

9. A method as in claim 7, further comprising providing a movable structure constructed and arranged to move in response to the patient's respiratory cycle, wherein movement of the movable structure in one direction stores the mechanical work done by the patient during the exhalation phase of the respiratory cycle of the patient and wherein movement of the movable structure in an opposite direction utilizes only the stored mechanical energy to assist patient respiratory effort during an inhalation phase of the respiratory cycle of the patient.

10. A method as in claim 9, further comprising powering the movable structure to pressurize a portion of at least one of an inspiration chamber and an exhalation chamber to assist the patient's respiratory effort.

11. A breathable air supply apparatus for a patient, comprising:
   movable means for drawing fresh air from the atmosphere into an inspiration chamber and allowing air exhaled by the patient to accumulate within an exhalation chamber in response to patient expiration during an exhalation phase of the respiratory cycle of the patient and for pressuring and providing the fresh air from the inspiration chamber to the patient at a substantially constant positive pressure and expunging the exhaled air accumulated within the exhalation chamber into the atmosphere in response to patient inspiration during an inhalation phase of the respiratory cycle of the patient;
   storage means for storing mechanical energy in the form of mechanical work done by the patient during the exhalation phase; and
   utilize means for utilizing only the stored mechanical energy to assist patient respiratory effort during the inhalation phase,
   wherein the storage means includes a weight that is at least partially determinative of the pressure.

12. A breathable air supply apparatus as in claim 11, wherein the utilize means comprises transfer means for transferring the stored mechanical energy from the storage means to assist respiratory effort during the inhalation phase of the respiratory cycle of the patient.

13. A breathable air supply apparatus as in claim 11, wherein movement of the movable means in one direction stores the mechanical work done by the patient during the exhalation phase of the respiratory cycle of the patient and wherein movement of the movable means in an opposite direction utilizes only the stored mechanical energy to assist patient respiratory effort during the inhalation phase of the respiratory cycle of the patient.

14. A breathable air supply apparatus as in claim 13, wherein the movable means is powered to pressurize a portion of at least one of an inspiration chamber and an exhalation chamber to assist the patient's respiratory effort.

15. A breathable air supply apparatus for a patient, comprising:
 a breathable gas supply system; and
 a respiratory mask assembly in communication with the breathable gas supply system, the breathable gas supply system being constructed and arranged to supply breathable gas from the atmosphere to the respiratory mask assembly and to remove exhaled gas into the atmosphere from the respiratory mask assembly;
 the breathable gas supply system comprising:
 a housing having an outer wall configured to define an air chamber;
 a first movable structure movable in the air chamber during the patient's respiration cycle, the movable structure being configured such that (1) the first movable structure is capable of storing mechanical energy in the form of mechanical work done by the patient during an exhalation phase of the respiratory cycle of the patient; and (2) the first movable structure is capable of transferring the stored mechanical energy to the patient during an inhalation phase of the respiratory cycle of the patient to provide a source of pressurized gas at a substantially constant positive pressure to assist the patient's respiratory effort,
 wherein the first movable structure includes a weight that is at least partially determinative of the pressure.

16. A breathable gas supply apparatus as in claim 15, further comprising a second movable structure constructed and arranged to move in phase with the patient's respiratory cycle.

17. A breathable gas supply apparatus as in claim 16, wherein at least one of the first movable structure and the second movable structure is powered to pressurize a portion of the air chamber to assist the patient's respiratory effort.

18. A breathable gas supply apparatus as in claim 16, wherein the first movable structure and the second movable structure are movable in a common direction during the inhalation phase of the respiratory cycle of the patient and are movable in a direction opposite the common direction during the exhalation phase of the respiratory cycle of the patient.

19. A breathable gas supply apparatus as in claim 15, wherein the outer wall includes a vent formed therein, the vent being in communication with an atmosphere surrounding the housing.

20. A breathable gas supply apparatus as in claim 19, wherein the first movable structure is a part of a pressure actuator assembly, the pressure actuator assembly further comprising a second movable structure, each of the first and second movable structures being constructed and arranged to move in response to fluid pressure between (1) a first position of each of the first and second movable structures, wherein movement of the first and second movable structures in a common direction facilitates a supply of exhaled gas being received into the air chamber from the respiratory mask assembly and facilitates a supply of breathable gas being received into the air chamber and (2) a second position of each of the first and second movable structures, wherein movement of the first and second movable structures in a direction opposite the common direction facilitates a supply of exhaled gas being supplied through the vent and facilitates a supply of breathable gas being supplied to the respiratory mask assembly.

21. A breathable gas supply apparatus as in claim 15, further comprising an air chamber dividing member operatively coupled to the outer wall, the air chamber dividing member being constructed and arranged to divide the air chamber into an inspiration chamber and an exhalation chamber, such that separate gases may be carried within each of the inspiration and exhalation chambers.

22. A breathable gas supply apparatus as in claim 21, wherein the first movable structure is movable between (1) a first position thereof, wherein the first movable structure is moved in a first direction within the air chamber in response to the patient's exhalation to supply exhaled gas to the exhalation chamber and to facilitate supply of a breathable gas to the inspiration chamber and (2) a second position thereof, wherein the first movable structure is moved in a direction opposite to the first direction within the air chamber in response to the patient's inhalation to facilitate exhalation of exhaled gas outside of the housing and to supply breathable gas to the patient.

23. A breathable gas supply apparatus as in claim 22, wherein the air chamber dividing member has a central opening formed therein.

24. A breathable gas supply apparatus as in claim 23, wherein the first movable structure comprises:
 a body portion extending through the central opening in the air chamber dividing member and being configured to move along the central opening;
 an upper end portion being disposed in the exhalation chamber and extending transverse to the body portion; and
 a lower end portion being disposed in the inspiration chamber and extending transverse to the body portion, substantially parallel to the upper end portion.

25. A breathable gas supply apparatus as in claim 21, further comprising:
 a first sealing structure in communication with the air chamber;
 a second sealing structure in communication with the air chamber; and
 a third sealing structure in communication with the air chamber,
 wherein the first sealing structure permits fluid communication therethrough during an exhalation phase of the respiratory cycle of the patient, but prevents gas to exit the inspiration chamber during an inhalation phase of the respiratory cycle of the patient,
 wherein the second sealing structure permits fluid communication therethrough during the inhalation phase of the respiratory cycle of the patient, but prevents gas to enter the inspiration chamber during the exhalation phase of the respiratory cycle of the patient, and
 wherein the third sealing structure permits fluid communication therethrough during the exhalation phase of the respiratory cycle of the patient, but prevents gas to exit the exhalation chamber during the inhalation phase of the respiratory cycle of the patient.

26. A breathable gas supply apparatus as in claim 15, further comprising an external power supply configured to supply power to the breathable gas supply system.

27. A breathable gas supply apparatus as in claim 15, wherein the respiratory mask assembly comprises a respiratory mask having an inspiration port and an exhalation port formed therein, the inspiration port constructed and arranged to form an entrance to the respiratory mask where a supply of breathable gas may enter therethrough and the exhalation port constructed and arranged to form an exit to the respiratory mask where a supply of exhaled gas may exit the respiratory mask therethrough.

28. A breathable gas supply apparatus as in claim 27, further comprising:
   an inspiration conduit configured to removably connect to the inspiration port and to an outlet of the breathable gas supply system configured to provide a supply of breathable gas therethrough; and
   an exhalation conduit configured to removably connect to the exhalation port and to an inlet of the breathable gas supply system configured to provide a supply of exhaled gas therethrough.

29. A breathable gas supply apparatus as in claim 15, wherein the first movable structure comprises flexible mechanical structure.

30. A breathable gas supply apparatus as in claim 29, wherein the flexible mechanical structure includes an inner flexible mechanical structure and an outer flexible mechanical structure.

31. A breathable gas supply apparatus as in claim 30, wherein one of the inner flexible mechanical structure and the outer flexible mechanical structure is powered to pressurize a portion of at least one of the inspiration chamber and the exhalation chamber to assist the patient's respiratory effort.

32. A breathable gas supply apparatus as in claim 30, wherein the housing includes an upper wall and a lower wall spaced from the upper wall, the inner flexible mechanical structure and the outer flexible mechanical structure being disposed between the upper wall and the lower wall of the housing.

33. A breathable gas supply apparatus as in claim 32, wherein each of the inner flexible mechanical structure and the outer flexible mechanical structure includes a concertina.

34. A breathable gas supply apparatus as in claim 29, wherein the inner flexible mechanical structure defines the inspiration chamber and the inner flexible mechanical structure and the outer flexible mechanical structure cooperate to define the exhalation chamber.

* * * * *

UNITED STATES PATENT AND TRADEMARK OFFICE
CERTIFICATE OF CORRECTION

| | | |
|---|---|---|
| PATENT NO. | : 8,881,723 B2 | Page 1 of 1 |
| APPLICATION NO. | : 10/270611 | |
| DATED | : November 11, 2014 | |
| INVENTOR(S) | : Robert H. Frater | |

It is certified that error appears in the above-identified patent and that said Letters Patent is hereby corrected as shown below:

In the Claims:

In Claim 5, column 17, line 66, "A breathable gas supply apparatus as in claim 4" should be corrected to --A breathable gas supply apparatus as in claim 2--.

Signed and Sealed this
Twenty-first Day of April, 2015

Michelle K. Lee
*Director of the United States Patent and Trademark Office*